US012736523B2

(12) United States Patent
Fong et al.

(10) Patent No.: US 12,736,523 B2
(45) Date of Patent: Sep. 15, 2026

(54) MAINTENANCE AND/OR CULTURE OF TISSUE SLICES IN VITRO OR EX VIVO

(71) Applicants: NATIONAL UNIVERSITY OF SINGAPORE, Singapore (SG); SINGAPORE HEALTH SERVICES PTE LTD, Singapore (SG)

(72) Inventors: Li Shan Eliza Fong, Singapore (SG); Christabella Adine, Singapore (SG); Narayanan Gopalakrishna Iyer, Singapore (SG); Elekuttige Anton Kanishka Fernando, Singapore (SG)

(73) Assignees: National University of Singapore, Singapore (SG); Singapore Health Services PTE LTD, Singapore (SG)

(*) Notice: Subject to any disclaimer, the term of this patent is extended or adjusted under 35 U.S.C. 154(b) by 299 days.

(21) Appl. No.: 18/555,348

(22) PCT Filed: Apr. 18, 2022

(86) PCT No.: PCT/SG2022/050226
§ 371 (c)(1),
(2) Date: Oct. 13, 2023

(87) PCT Pub. No.: WO2022/220757
PCT Pub. Date: Oct. 20, 2022

(65) Prior Publication Data

US 2024/0201170 A1 Jun. 20, 2024

(30) Foreign Application Priority Data

Apr. 16, 2021 (SG) ............................ 10202103937S

(51) Int. Cl.
*G01N 33/50* (2006.01)
*C12N 5/09* (2010.01)

(52) U.S. Cl.
CPC ....... *G01N 33/5011* (2013.01); *C12N 5/0693* (2013.01); *G01N 33/5082* (2013.01); *C12N 2500/50* (2013.01); *C12N 2501/727* (2013.01); *C12N 2533/50* (2013.01); *C12N 2533/80* (2013.01); *C12N 2537/10* (2013.01); *G01N 2500/10* (2013.01)

(58) Field of Classification Search
None
See application file for complete search history.

(56) References Cited

U.S. PATENT DOCUMENTS 6,790,638 B1 * 9/2004 Carosella ........... A61K 39/0011 435/7.2
7,678,758 B2 * 3/2010 Lamb ..................... A61K 40/11 514/19.3
2009/0221444 A1 * 9/2009 Borlak ............. G01N 33/57423 435/6.12
2012/0039857 A1 2/2012 Smith et al.

FOREIGN PATENT DOCUMENTS

| | | | |
|---|---|---|---|
| CN | 107217039 A | | 9/2017 |
| CN | 107217039 | * | 3/2020 |
| CN | 112195152 A | | 1/2021 |
| WO | 2014113573 A1 | | 7/2014 |
| WO | 2019113026 A1 | | 6/2019 |

OTHER PUBLICATIONS

International Search Report and Written Opinion from corresponding PCT/SG2022/050226, mailed May 17, 2022 (15 Pages).
Hubkak, K.M., "Novel Biomimetic Hydrogels for Glandular and Tumor Tissue Engineering", PHD thesis submitted to Rice University, May 1, 2020, pp. 22, 23, 102, and Figure 3.
Nicolas, J. et al., "3D Extracellular Matrix Mimics: Fundamental Concepts and Role of Materials Chemistry to Influence Stem Cell Fate", Biomacromolecules, Jun. 8, 2020, vol. 21, No. 6, pp. 1968-1994, 1978 and Figure 6.
Yangz et al., "Designer Self-Assembling Peptide Hydrogels to Engineer 3D Cell Microenviroments for Cell Constructs Formation and Precise Oncology Remodeling in Ovarian Cancer", Adv Sci (Weinh), Mar. 20, 2020, vol. 7, No. 9 (19037818), pp. 1-30.
Extended European Search Report for European Patent Application No. 22788568.8.
Zarembinski et al., "HyStem, a customisable hyaluronan-based hydrogel matrix for 3D cell culture", DOI: 10.1002/9781118851647.ch8.
Fong et al., "Hydrogel-Based 3D Model of Patient-Derived Prostate Xenograft Tumors Suitable for Drug Screening", DOI: 10.1021/mp500085p.
Gajendiran et al., "Recent Developments in Thiolated Polymeric Hydrogels for Tissue Engineering Applications", DOI: 10.1089/ten.teb.2016.0442.

* cited by examiner

*Primary Examiner* — Blaine Lankford
(74) *Attorney, Agent, or Firm* — Thomas Horstemeyer, LLP.

(57) ABSTRACT

The present invention relates to the maintenance and/or culture of tissue slices in vitro or ex vivo. In particular, the present invention relates to a method for the maintenance and/or culture of tissue slices using hydrogels. In one embodiment, the hydrogel is a semi-synthetic hydrogel comprising thiolated hyaluronan with acrylated peptides comprising KGGGPQGIWGQGK (SEQ ID NO: 1) that are degradable by matrix metalloproteinases. In particular, the present invention provides a platform suitable for downstream analysis such as real-time imaging, other real-time study of the tissue in culture and testing of a therapeutic agent or a potential therapeutic agent.

16 Claims, 21 Drawing Sheets

Specification includes a Sequence Listing.

```
                         SEQUENCE LISTING


<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Conjugated peptide sequence KGGGPQGIWGQGK

<400> SEQUENCE: 1

Lys Gly Gly Gly Pro Gln Gly Ile Trp Gly Gln Gly Lys
1               5                   10


<210> SEQ ID NO 2
<211> LENGTH: 5
<212> TYPE: PRT
<213> ORGANISM: Artificial
<220> FEATURE:
<223> OTHER INFORMATION: Conjugated peptide sequence GRGDS

<400> SEQUENCE: 2

Gly Arg Gly Asp Ser
1               5
```

MAINTENANCE AND/OR CULTURE OF TISSUE SLICES IN VITRO OR EX VIVO

FIELD OF THE INVENTION

The present invention relates to the maintenance and/or culture of tissue slices in vitro or ex vivo. In particular, the invention relates to the maintenance and/or culture of tumour slices. The tumour slices may be used for study of cancer/tumour biology and in particular personalized drug testing.

BACKGROUND OF THE INVENTION

For the study of cancer/tumour biology, an understanding of the complex in vitro environment of the tumour/cancer is important. For example, the field of personalised oncology is on rapid ascent with the advent of tumour organoid technologies which recapitulate cancer cell heterogeneity in patient tumours (Drost and Clevers, 2018). However, these cancer organoid models are inherently too simple as they lack many components of the tumour microenvironment (TME) compared to the highly complex and heterogeneous matrix and stromal landscape in patient tumours (Tang et al., 2021). Although there have been efforts to incorporate the tumour stroma into organoid-based cultures (Cattaneo et al., 2020), these models do not account for stromal heterogeneity and the unique spatial distribution of extracellular matrix, cancer and stromal cells; all of which are important parameters that influence tumour progression and the efficacy of TME-targeting drugs, especially immune checkpoint inhibitors (ICIs) (Bruni et al., 2020).

On the other end of the tumour modeling spectrum, humanized (patient-derived xenograft) PDX mice have been developed for the assessment of immunotherapies but they are typically costly, low-throughput and time-consuming to establish. Ex vivo patient-derived tumour explant cultures (including tumour slices) involve the culture of fragments of resected human tumours that potentially retain the entire TME of the original tumour. Although there is strong evidence for their ability to predict patient response to chemotherapy, these platforms have not been widely adopted in translational research likely because of the exponential use of cancer cell lines, organoids and PDX model systems (all of which can be maintained for longer periods of time) in the past few decades (Rowley et al., 2020). However, with the growing recognition of the importance of patient-specific TME in mediating drug response in patient tumours, especially for ICI, there is an urgent need to revive patient-derived tumour slice models for the evaluation of TME-targeting strategies and delineating mechanisms of resistance.

While advantageous in many aspects, subject-derived explant cultures are limited by poor tissue viability ex vivo; typically the tissue disintegrates within a short time-frame of about 3 to 6 days (Gerlach et al., 2014). This makes it highly challenging to conduct drug testing and mechanistic studies which require longer durations in culture. It is generally thought that a key contributing factor to decreased viability over time in culture is hypoxia, following the removal of tumour tissue from the blood supply (Davies et al., 2015). It remains highly challenging to prolong the maintenance and culture of such subject-derived explant cultures.

Current methods of culturing subject-derived explant cultures or tumour slices typically rely on the use of artificial substrates, such as floating slice culture in a petri dish, or the use of PTFE cell culture inserts (most widely used) for mechanical support. While these culture conditions enable the culture of tumour slices for a few days, the culture substrate is not optimized to the specific requirements of the tissue to maintain/culture the explant or tumour slices.

Patent CN107217039B describes a method that enables 3D culture of tumour tissue using hydrogels and compares hydrogel with Matrigel and Vitro-gel 3D RGD as culture matrices. According to this patent, the use of hydrogel enables better fixation of the tumour tissue to plastic dish, is of lower cost and is simpler to handle as compared to Matrigel. An optimized medium for culturing tissues from a few cancer types is also described. However, there is no mention of the composition of the hydrogel used in this patent, except that it is a synthetic peptide bionanomaterial. More importantly, in this described method, it appears that the tumour piece is completely embedded in three-dimensions (3D) within the culture matrix.

Additionally, this patent describes a method utilizing tumour pieces cut by ophthalmological instruments, which generates tumour pieces with non-uniform surface areas and sizes which may not be suitable for downstream analysis such as real-time imaging and other real-time study of the tissue in culture. Moreover, this patent described a very limited downstream analysis process, which involves fixation of the tissue in hydrogel for immunohistochemistry or immunofluorescence.

The culture of normal lung tissue slices embedded in hydrogel has been reported by Bailey et al., (2020). However, in this paper, the tissue slice is completely sandwiched between two layers of hydrogel.

Further, Salas et al. (2020) reported the use of unmodified alginate scaffolds to culture tumour slices for uterine leiomyoma.

Overall, it is highly desirable to address the limitations of existing methods of culturing tumour tissues ex vivo or in vitro, suitable for downstream analysis.

SUMMARY OF THE INVENTION

According to a first aspect, the present invention provides a method for maintaining and/or culturing tissue slice; comprising:

(i) providing a tissue slice;
(ii) providing a hydrogel comprising conjugated peptides;
(iii) placing the tissue slice onto the hydrogel comprising conjugated peptides; and
(iv) maintaining and/or culturing the tissue slice on the hydrogel using a culture medium.

Importantly, it will be appreciated that the biochemical and biophysical properties of the hydrogels may be modulated (tunable or adapted) for the optimal maintenance and/or culture of the different types of tissue slices. The method of the present invention may be used for maintaining and/or culturing any tissue slice. For example, the tissue slice may be from a tumour. Accordingly, the present invention may be used for maintaining and/or culturing a tumour slice. It will further be appreciated that the method preserves the composition of the tissue slice or tumour slice, in particular, the cell composition of the tissue slice or tumour slice is preserved.

Any suitable hydrogel may be used for the present invention. Suitable hydrogels include but are not limited to a polymer, a synthetic hydrogel, a semi-synthetic hydrogel.

It will also be appreciated that the conjugated peptides of the hydrogel may be for crosslinking the hydrogel and/or presenting biochemical cues.

DEFINITIONS

Figure 1:
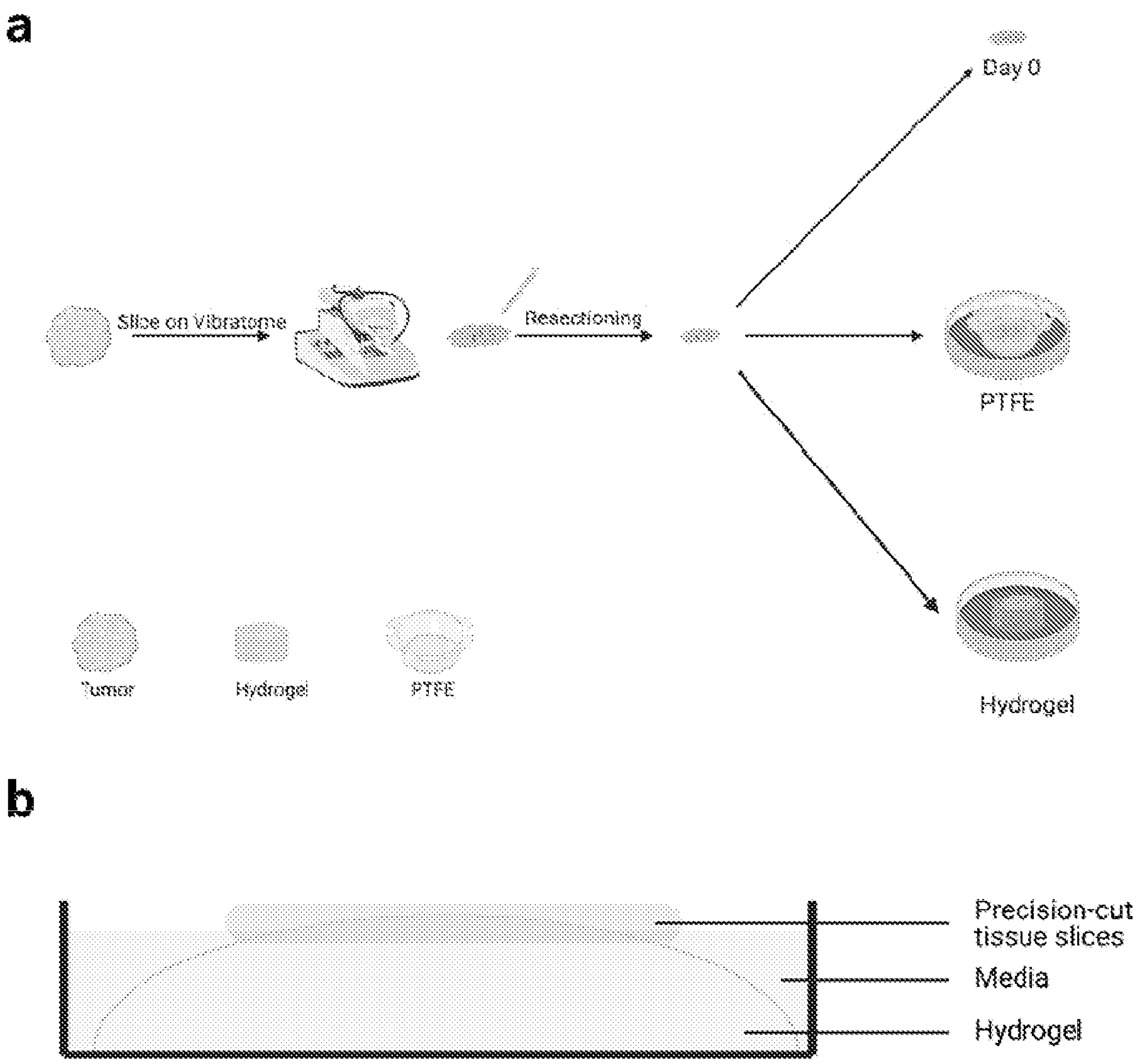
FIG. 1. Schematic diagram of (a) workflow and (b) the hydrogel culture configurations for tumour slices. The tumour slices were partially submerged while layered on the HA hydrogel and thus an air-liquid interface is established.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

As used herein, biochemical cues refer to cues that cells respond to in their interaction with the culture substrate/material. These cues may or may not be present in the natural extracellular matrix. Biochemical cues are typically cell surface proteins or extracellular matrix proteins (natural or synthetic), or parts of cell surface proteins or extracellular matrix proteins (natural or synthetic). For example, biochemical cues include but are not limited to RGD peptide or other peptide sequences from collagen, laminin, fibronectin or perlecan, or the entire peptide/protein.

DETAILED DESCRIPTION OF THE INVENTION

Bibliographic references mentioned in the present specification are for convenience listed in the form of a list of references and added at the end of the examples.

According to a first aspect, the present invention provides a method for maintaining and/or culturing tissue slices; comprising:

(i) providing a tissue slice;
(ii) providing a hydrogel comprising conjugated peptides;
(iii) placing the tissue slice onto the hydrogel comprising conjugated peptides; and
(iv) culturing the tissue slice on the hydrogel comprising conjugated peptides using a culture medium.

Importantly, it will be appreciated that the biochemical and biophysical properties of the hydrogels may be modulated (tunable or adapted) for the optimal maintenance and/or culture of the different types of tissue slices. The method of the present invention may be used for maintaining and/or culturing any tissue slice. For example, the tissue slice may be from a tumour. Accordingly, the present invention may be used for maintaining and/or culturing a tumour slice. It will further be appreciated that the method preserves the composition of the tissue slice or tumour slice, in particular, the cell composition of the tissue slice or tumour slice is preserved.

Any suitable hydrogel may be used for the present invention. Suitable hydrogels include but are not limited to a polymer, a hydrogel, or a semi-synthetic hydrogel. As an example, the polymer may be a natural polymer hydrogel. In particular, the natural polymer hydrogel may be an alginate hydrogel.

An example of a suitable synthetic hydrogel may comprise a synthetic polymer. In particular, the synthetic polymer may comprise poly(ethylene glycol).

As a further example, a suitable semi-synthetic hydrogel may comprise a natural polymer modified with at least one chemical group. In particular, the semi-synthetic hydrogel may comprise hyaluronan, collagen or gelatin modified with at least one chemical group. For example, the chemical group may be for crosslinking the hydrogel. The modification may be with a chemical group comprising a thiol and/or an acrylate group.

It will be appreciated that the peptides may be conjugated to the hydrogel backbone.

According to a further aspect, the semi-synthetic hydrogel comprises thiolated hyaluronan with conjugated peptides.

It will further be appreciated that the conjugated peptides of the hydrogel may be for crosslinking the hydrogel and/or presenting biochemical cues. Peptides for crosslinking the hydrogel may comprise degradable or non-degradable peptide sequences. The hydrogel for the invention may also comprise polymeric crosslinkers for crosslinking the hydrogel. An example may be poly(ethylene glycol)-diacrylate. Accordingly, the polymeric crosslinkers may or may not be peptide crosslinkers.

It will be appreciated that the crosslinking may be physical interactions, covalent bonding or non-covalent bonding.

Accordingly, the hydrogel may comprise peptides degradable by matrix metalloproteinases or other proteases. For example, the peptides biodegradable by matrix metalloproteinases or other proteases may comprise the sequence PQ. In particular, said peptide may comprise the sequence KGGGPQGIWGQGK (SEQ ID NO: 1) or a scrambled derivative.

The hydrogel comprising peptides degradable by matrix metalloproteinases or other proteases may further comprise at least one further set of peptides. The at least one further set of peptide may present/provide biochemical cues. As an example, the at least one further set of peptides comprise one or more types of extracellular matrix protein or peptides comprising a peptide sequence derived from an extracellular matrix protein. For example, said extracellular matrix protein includes but is not limited to fibronectin, collagen and/or laminin.

In a further example, the at least one further set of peptides comprises the sequence RGD or a scrambled derivative. In particular, the at least one further set of peptides comprises the sequence GRGDS (SEQ ID NO: 2) or a scrambled derivative. It will be appreciated that the RGD confers cell adhesive properties to the hydrogel.

Alternatively, the peptides for any aspect of the present invention may comprise one or more types of extracellular matrix protein, or peptides comprising a peptide sequence derived from an extracellular matrix protein. For example, said extracellular matrix protein includes but is not limited to fibronectin, collagen and/or laminin. In particular, the peptides comprise the sequence RGD or a scrambled derivative. More in particular, the peptide comprise the sequence GRGDS (SEQ ID NO: 2) or a scrambled derivative.

The peptides of any aspect, example or embodiment of the present invention may comprise acrylated peptides.

It will be appreciated that physical or mechanical cues refers to cues sensed by cells leading to mechanotransduction signaling. These cues may be provided in the natural extracellular matrix in vivo. In the present invention, it will be appreciated that physical or mechanical cues includes but is not limited to stiffness and stress-relaxation properties of the hydrogel.

Where the hydrogel comprises a polymer, attaining the desired stiffness of the hydrogel comprising conjugated peptide depends on the concentration of the polymer. It will be appreciated varying the concentration of the polymer in the hydrogel is one way to vary the stiffness of the hydrogel. An alternative way of attaining the desired stiffness of the hydrogel comprises or further comprises increasing or decreasing the concentration of crosslinkers in the hydrogel.

It will be appreciated that where the hydrogel requires crosslinking or comprises crosslinkers, the tissue slice may be placed on the hydrogel as crosslinking of the hydrogel occurs for achieving mechanical fixation of the tissue slice in the hydrogel.

As a further aspect of the method of the present invention, step (iv) maintaining and/or culturing the tissue slice on the hydrogel using a culture medium comprises contacting the hydrogel with the culture medium. In particular, contacting the hydrogel with the culture medium comprises substantially submerging or partially submerging the hydrogel with the culture medium. More in particular, the hydrogel is substantially submerged and the tissue slice is partially submerged with the culture medium.

Any suitable culture medium may be used for maintaining and/or culturing the tissue slice. In particular, the culture medium may comprise at least one ROCK inhibitor.

It will also be appreciated that where the cultured tissue slices require characterization, the tissue slice may be subjected to single-cell studies such as single-cell RNA sequencing to determine composition and gene expression changes in the cultured tissue slice.

As a further aspect of the method of the present invention, further analyses such as multi-dimensional flow cytometry or multiplex immunofluorescence staining can be performed.

Having now generally described the invention, the same will be more readily understood through reference to the following examples which are provided by way of illustration, and are not intended to be limiting of the present invention.

It will be appreciated that a plurality of tissue slices may be cultured with each tissue slice on a portion of the hydrogel or each tissue slice on a separate hydrogel.

Each tissue slice may be of substantially uniform thickness.

The method of the present invention may further comprises direct real-time imaging of the tissue slice. In addition, the method of the present invention may further comprise testing the effect of at least one therapeutic agent or potential therapeutic agent on the tissue slice. In particular, the at least one therapeutic agent or potential therapeutic agent may be an immune checkpoint inhibitor. It will appreciated that a therapeutic agent or a potential therapeutic agent may be tested individually or in combination with one or more other therapeutic agent or potential therapeutic agent. For example, an immune checkpoint inhibitor may be tested individually or tested in combination with one or more other immune checkpoint inhibitor. An immune checkpoint inhibitor may be tested in combination with one or more other therapeutic agent. For example, the method comprises comparing a tissue slice culture in a culture medium comprising at least one therapeutic agent or potential therapeutic agent with a tissue slice cultured in culture medium without the therapeutic agent or potential therapeutic agent. It will be appreciated that two or more therapeutic agent or therapeutic agents may be tested and compared.

EXAMPLES

Example 1 Materials and Methods

HNSCC Patient Tumours

Resected tumour samples were collected from National Cancer Center Singapore (NCCS, Singapore) with written consent obtained from patients and in strict accordance with the institutional ethical guidelines of NCCS. The study was approved by National University of Singapore Institutional Review Board (NUS IRB). Fresh specimens were collected from a total of 15 patients over a two-year period, along with relevant de-identified clinical data.

Tumour Slice Preparation

Primary tumour samples were obtained from surgical specimens in the head and neck squamous cell carcinoma (HNSCC) patients who underwent curative surgery. Tumours were resected from patients from the National Cancer Centre Singapore. Tumour tissues were collected and transported in 4° C. chilled 1× Hanks' Balanced Salt Solution (HBSS, Sigma) with Penicillin-Streptomycin (100 U/mL), Amphotericin B (0.25 μg/mL), and Gentamicin (10 μg/mL) (Gibco, Thermofisher). Tumour tissues were processed within 2-5 h after removal from the patient. Tumour tissues were then washed with sterile HBSS 3 times. Tumour tissue slices were prepared at a thickness of 300 μm using the precision-cut vibrating-blade microtome (Leica VT1200S) and randomized before distribution into groups. The tissue slices were cultivated in supplemented Dulbecco's Modified Eagle Medium/Nutrient Mixture F-12 medium for 3 h.

Culture Configurations for Tumour Slices

In this example, tissue slices were maintained either submerged in medium (floating), or placed/layered on Millicell Cell Culture inserts (PTFE, Merck Millipore), or placed/layered directly on different hydrogel configurations. Each different hydrogel configuration comprises thiolated hyaluronan (HA) as the backbone polymer, with defined acrylated peptide sequences for crosslinking the hydrogel. For floating condition, slices were placed in 12- or 24-well plate and medium was added to submerge the slices completely. For PTFE culture, slices were layered on the PTFE membrane, and medium was added up to the level of the membrane. For tumour slice culture using hydrogel, hyaluronan (HA)-based hydrogels were used. The hydrogel itself comprises thiolated hyaluronan, acrylated GRGDS (SEQ ID NO: 2) (73.7 mg/ml) and acrylated PQ peptides (40 mg/ml) at a volume ratio of 4:1:1 respectively. PQ represents the amino acid sequence, KGGGPQGIWGQGK (SEQ ID NO: 1), that is degradable by matrix metalloproteinases. Peptides were conjugated to acryl-PEG using SVA-PEG-acryl (Laysan Bio) in a reaction between NHS esters and amines. Acrylated PQ peptides serve as the crosslinker as the acrylate groups flanking the PQ peptide react with thiols on HA via a Michael addition reaction. Hydrogels can be changed in stiffness by modulating HA concentration (e.g. 1, 2, 3%) or by changing concentration of the PQ crosslinker. Additionally, different biochemical cues can be conjugated to hydrogel besides RGD, such as peptide sequences from collagen or laminin. Hydrogel solutions (30-50 μL) were pipetted into well-plates and following which, tumour slices were placed/layered on top during hydrogel crosslinking; the hydrogels were allowed to crosslink for full 1 h before culture medium was added (to the level of the tissue slice but not submerging the tissue slice). It is important to layer the tumour slice while the hydrogel is crosslinking (and not after crosslinking is over) to ensure that the hydrogel solution 'wraps' around the tumour slice and prevents the tumour slice from detaching off the hydrogel during culture (FIG. 1B).

Culture medium was supplemented with 10 μM ROCK inhibitor (StemCell Technologies) for 1 day. Subsequently, culture medium was replaced every 2 days. Slices were collected at various time points, either stained with viability dye or fixed in 10% neutral buffered formalin for H&E and immunohistochemistry (IHC). Gross tissue images were taken daily and analysed using ImageJ to measure tissue area shrinkage.

Hydrogel Fabrication

In this example, tissue slices were maintained either submerged in medium (floating), or layered on Millicell Cell Culture inserts (PTFE, Merck Millipore), or placed/layered directly on different HA hydrogel configurations. The hydrogel consists of thiol-modified HA crosslinked using functionalized acrylated peptides. Hydrogels can be modulated in stiffness by changing bulk HA polymer concentration or by changing the concentration of crosslinker. RGD (or the scrambled version, RDG) was conjugated to the HA hydrogel to confer integrin-binding, cell-adhesive properties.

Layering/Placing Tumour Slices on Crosslinking Hydrogel

In this example, hydrogel solutions were pipetted into well-plates and following which, tumour slices were placed/layered on top during hydrogel cross-linking. Culture medium was supplemented with 10 μM ROCK inhibitor (StemCell Technologies) for 1 day. Subsequently, culture medium was replaced every 2 days.

Live-Imaging for Viability

At each designated timepoint, tumour slices were treated with Calcein-AM, Propidium Iodide and Hoescht before slices were imaged with a confocal microscope. Slices in hydrogels were carefully transferred to a glass-bottom dish for direct imaging. Images were assessed by quantification of the total number of nuclei, and percentage of propidium iodide-positive cells using a spot detection algorithm.

Quantification of Tumour Slice Area

Gross tissue images were taken daily and analysed using ImageJ to measure tissue area shrinkage relative to Day 0.

Hematoxylin and Eosin Staining

Fixed tissue slices were collected, embedded in paraffin blocks, and sectioned. For examination of histopathology, paraffin sections were stained with hematoxylin and eosin. Briefly, sections were de-waxed in xylene and rehydrated in graded ethanol, followed by incubation with dyes. Sections were then dehydrated, cleared in xylene, and mounted.

Single-Cell RNA Sequencing Analysis

To obtain a single-cell expression atlas of cultured HNSCC tumour slices, single cell suspensions from dissociated tumour slices were combined with a master mix for reverse transcription, Single Cell 5' Gel Beads and Partitioning Oil on Chromium Chip A. The chip was loaded into a 10× Chromium Controller to partition single cells to generate Gel Beads-in-Emulsion (GEM). After the generation of GEMs, cells were lysed and mixed with reagents within corresponding GEMs and reverse transcribed for first-strand cDNA synthesis. Then, GEMs were broken and pooled for downstream cleanups to construct Illumina-ready libraries, each with a unique Chromium i7 library barcode for multiplexing purposes. Library was sequenced on a HiSeq system. The objective of single-cell analyses is to identify the different cellular types and subtypes within tumour slices. Cell Ranger pipelines from 10× Genomics were used to perform alignment and generate feature-barcode matrices of UMI counts. Clustering and gene expression analysis were performed using Seurat package. Genes expressed in less than 3 cells were filtered out, as well as cells with less than 200 detected genes or more than 10% mitochondrial genes. The remaining good quality cells were then clustered using Seurat and differentially expressed genes generated for each cluster. Cancer and stromal cell clusters were then identified based on differentially expressed genes.

Bulk RNA Sequencing and Analysis

Dissociated tumour slices were sequenced at the Duke-NUS Genome Biology Facility (DGBF). Bulk RNA sequence alignment and conversion to counts (--sjdbOverhang 149) were done using the STAR software, by mapping to the hg38 reference genome (homo_sapiens_hg38). Next, to determine the differentially expressed genes (DEGs), DESeq2 was used with the default settings. Log fold change shrinkage was carried out using the apeglm package. Significantly upregulated genes were determined by filtering for those with adjusted p value less than 0.05, and DEG heatmaps of the scaled CPM were plotted with ComplexHeatmap. To analyse YAP activity, a list of HNSCC-relevant YAP targets was obtained from Hiemer et al., (2015); while apoptosis markers were obtained from molecular signatures database's (mSigDB) hallmark apoptosis gene set. For gene set enrichment analysis (GSEA), genes were ranked by decreasing log 2 fold change and analysed using clusterProfiler's GSEA function at the default settings. Gene sets were obtained from the Gene Ontology Biological Processes (GO:BP) collection in mSigDB. Only enriched GO:BPpathways with False Discovery Rates of less than 0.05 were included. Dot plots were constructed with ggplot2. All statistical analyses and figure plots were done on R.

Immunohistochemistry and Immunofluorescence

H&E staining and dual IHC were performed on drug-treated and untreated HNSCC slices. Briefly, slices were fixed, processed using the automatic tissue processor, and embedded in paraffin. Paraffin blocks were sectioned and H&E staining was performed. Dual IHC was performed using ChromoPlex 1 Dual Detection (Leica DS9665) with a high pH EDTA-based buffer (ER2, Leica AR9640) for 20 min. A specific cocktail of antibodies was used to identify cancer cell apoptosis, including pan-cytokeratin and cleaved caspase-3 antibody. Standard immunofluorescence were performed with active YAP1. Image acquisition was done using the slide scanning system. The images were processed with a customized analysis profile using the nuclear segmentation method to quantify the percentage of apoptotic cancer cells.

Multiplex Immunofluorescence

Tumour slices at each timepoint were fixed and sections were generated. Following which, sections were stained with a panel of cancer and stromal markers (pan-CK, PDPN, SMA, CD31, CD68 and CD8).

Flow Cytometry

Tumour slices were first manually removed from the hydrogel and digested. Dissociated cells were spun down, washed, and resuspended, and counted using a cell counter. Prior to fixing, cells were stained for surface proteins with fluorophore-conjugated antibodies and fixable dye. The cell suspension were then washed with and fixed. Compensation was performed using single stains; live cells and singlets were gated by gating on a dye differentiating live and dead cells or on scatter characteristics or both.

Figure 2:
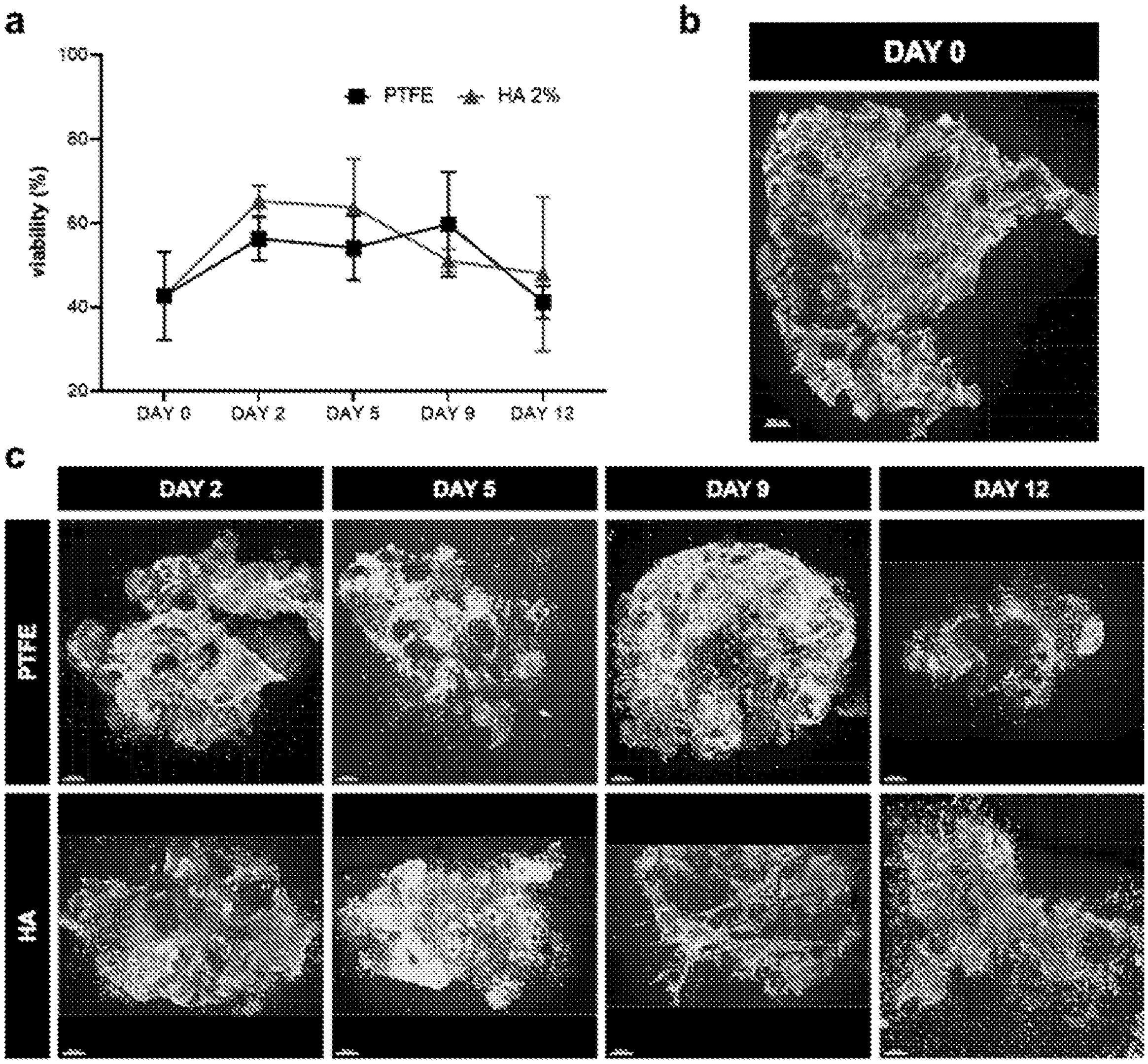
FIG. 2. HNSCC tumour slices stained with Calcein-AM and Propidium Iodide to stain live and dead cells in real time respectively. (A) Quantification of propidium iodide-positive enables calculation of % live-cells over time. While viability of tumour slices decline after 9 days in PTFE (black line), the decline is reduced in HA hydrogels (blue line). (B and C) Images depict confocal-imaged tumour slices at Day 0, 2, 5, 9 and 12 days grown on PTFE cell culture inserts or on HA hydrogels.
Figure 3A:
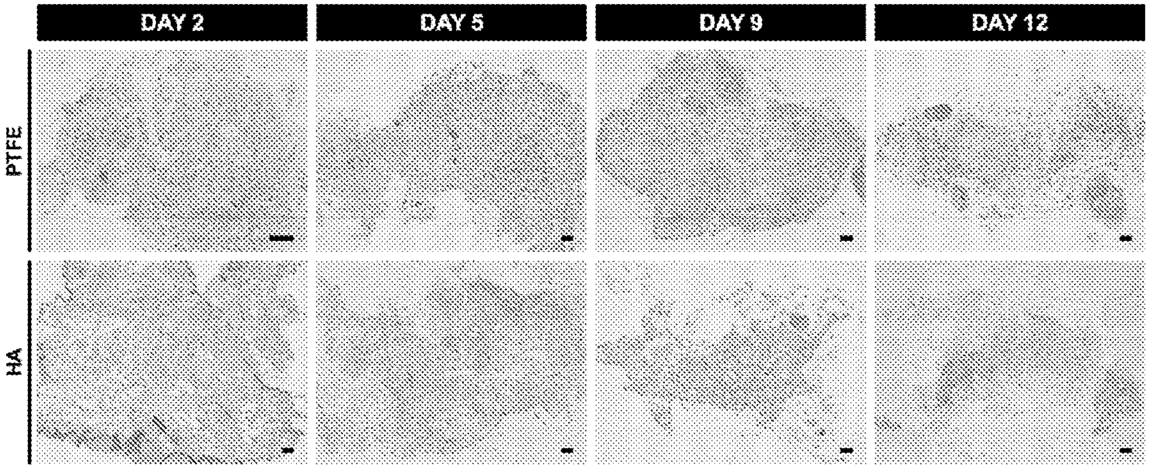
FIGS. 3A and 3B. Upon assessment of morphology by a pathologist, hematoxylin and eosin-stained tissue sections showed no significant differences (FIG. 3A) between, or superiority in morphology of (FIG. 3B), tumour slices cultured on HA hydrogel compared to PTFE cell culture inserts. This suggests that HA hydrogel is at the very least, comparable to current conventionally-used PTFE cell culture inserts for maintenance of tumour slice ex vivo.
Figure 3B:
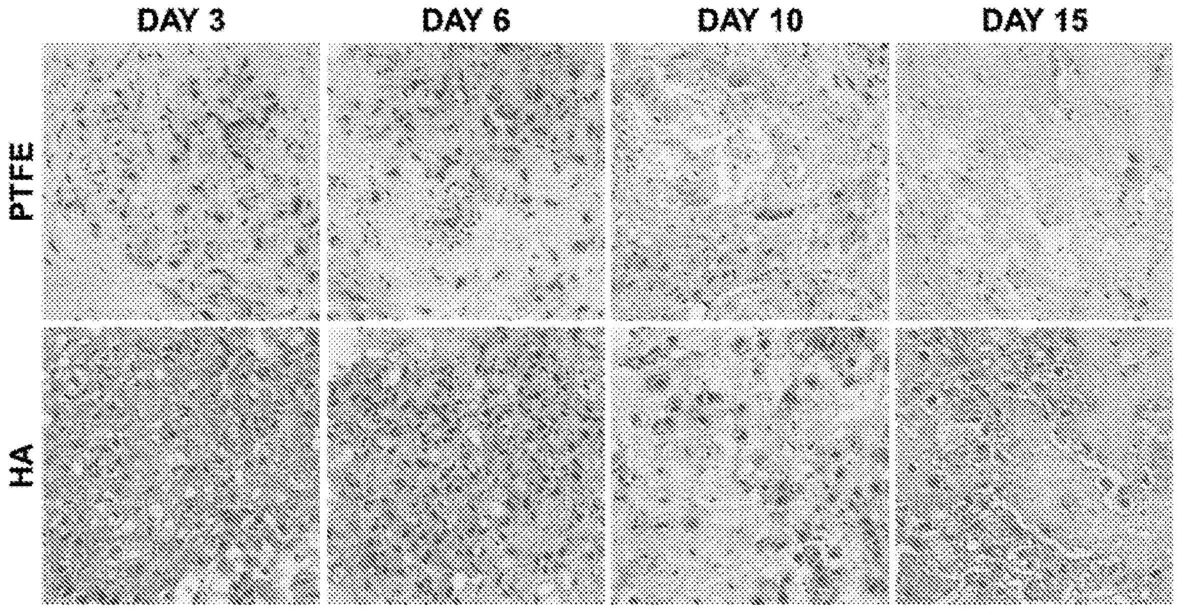

Example 2. Results 2.1 Engineered Hydrogel Better Preserves Tumour Slice Area Compared to PTFE Over Time In a preliminary study, hydrogel was observed to maintain viability of tumour size over at least 9 days (FIG. 2). It was also observed that the tumour slice in HA hydrogels is morphologically comparable (FIG. 3A) or superior (FIG. 3B) to PTFE across time.

Figure 4:
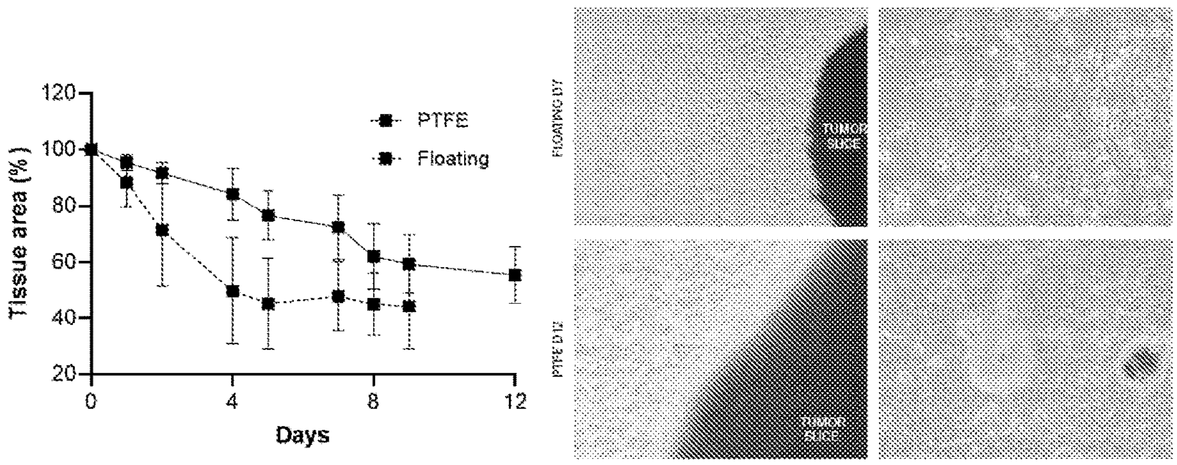
FIG. 4. Effect of underlying support on tumour slice area (measure of cellularity). (A) Quantification of changes in tumour slice area over time. Slices were cultured either floating (no support) or with the use of PTFE cell culture inserts. Greater shrinkage of tissue slice area was observed in the floating condition, suggesting the importance of providing physical support of tumour slices in culture. Bright field images taken of slices show efflux of cells from the cultured tissues in the different culture configurations (floating and PTFE).

The two most commonly used culture configuration, floating and the use of PTFE cell culture inserts were also compared to determine would be observable and measurable differences. Strikingly, when tumour slices were cultured in the absence of any underlying support (floating), a rapid decrease in tumour slice area was observed over 12 days. This shrinkage of tissue was significantly less pronounced when the tumour slices were cultured on PTFE (FIG. 4). This suggests that the provision of an underlying matrix support may reduce the extent of unwanted cell loss from the tumour slice, and hence preserve tumour tissue volume. It could not be determined whether this tissue shrinkage was due to cell loss or contraction of the ECM. However, it was observed that in both culture configurations, cells were found adhered on the culture plate for the floating condition, and on the PTFE membrane surface (FIG. 4). This suggests that the provision of an underlying matrix support may reduce the extent of unwanted cell loss from the tumour slice, and hence preserve tumour tissue volume.

Figure 5:
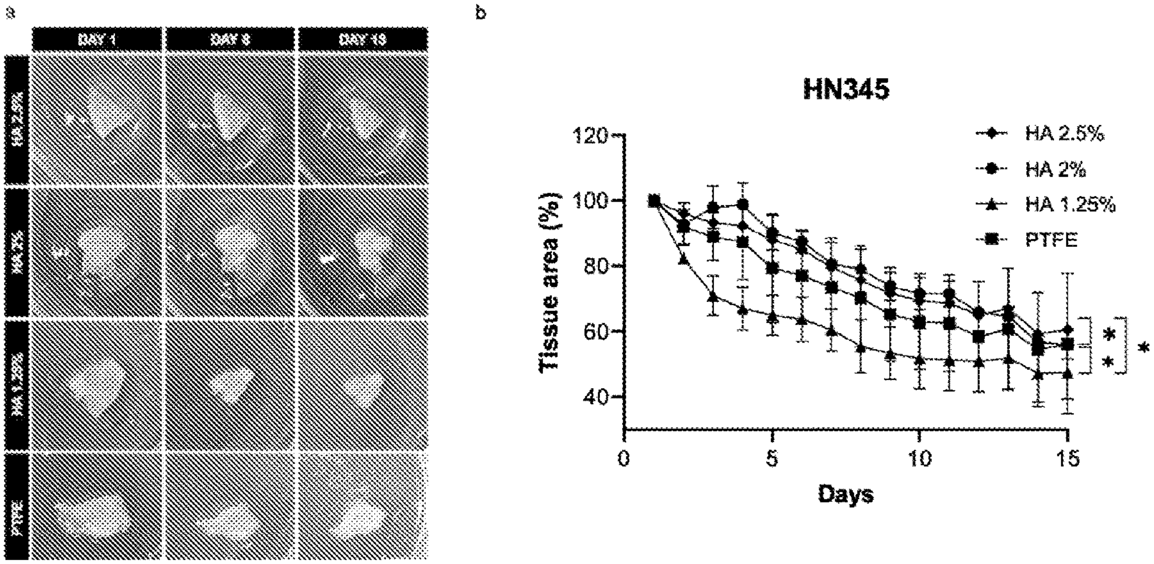
FIG. 5. HA hydrogels with varying stiffnesses were fabricated to determine whether hydrogel stiffness plays a role in maintaining tumour slice (HN 345) viability ex vivo. To change hydrogel stiffness, HA concentration was varied from 1.25% to 2.5% while keeping concentrations of RGD and PQ cross-linker the same. Upon assessment of tissue area, it was found that tumour slices on 1.25% HA hydrogels (less stiff) shrank more rapidly than that on 2% and 2.5% HA hydrogels. All data presented are from HNSCC patient tumours. PTFE cell culture inserts (PTFE) were used as reference in all experiments. Left: Images of tumour slice area tracked over 2 weeks in culture. Greater shrinkage of tissue is observed for slices on 1.25% HA hydrogels and PTFE compared to 2% hydrogels. Right: Quantification of tumour slice area (% of Day 0) shows more rapid decrease in tumour slice area for slices cultured on 1.25% HA hydrogels and PTFE compared to 2% HA hydrogels. 2% HA hydrogels significantly better preserve ($p<0.05$) tumour slice area as compared to PTFE and 1.25% HA hydrogels. * represents $p<0.05$.
Figure 6:
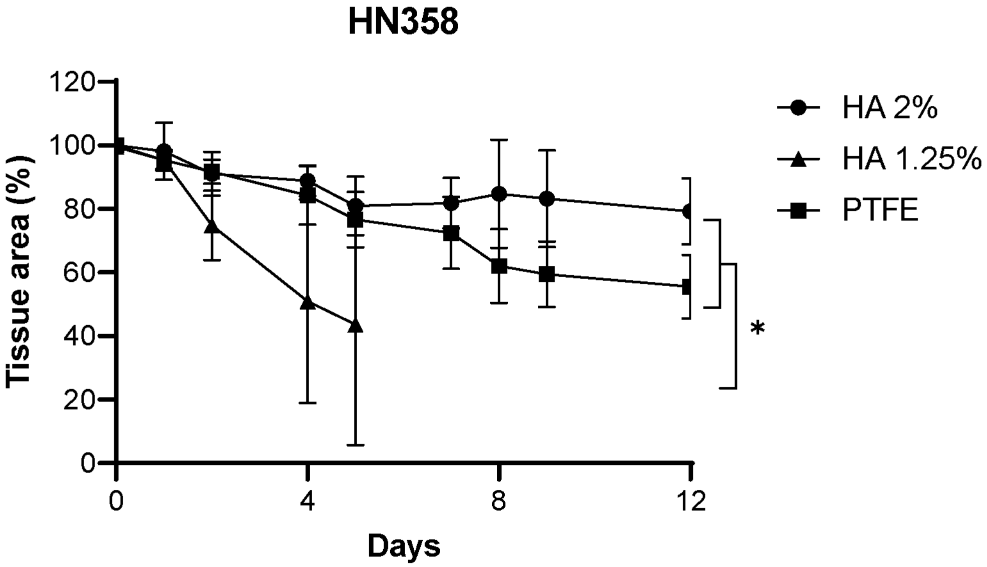
FIG. 6. Consistent with data in FIG. 5, 2% HA hydrogels best preserves tumour slice area (for another patient tumour, HN358) as compared to 1.25% HA hydrogels and PTFE cell culture inserts. * represents $p<0.05$.

The effect of HA hydrogel stiffness and adhesivity on slice viability was investigated. To modulate hydrogel stiffness, the bulk polymer concentration was changed while keeping the crosslinker concentration constant. Using preservation of tumour slice area as a surrogate measure of whether tumour tissue volume is maintained, tumour slices were cultured on 1.25%, 2% or 2.5% HA hydrogels as well as on PTFE cell culture inserts, which was used for all experiments in this study for reference. As shown in FIG. 5, a clear reduction in tissue area was observed for all conditions; however, the decrease was significantly more drastic in the 1.25% group. On the other hand, 2% HA hydrogels best preserved tumour slice area over time, even better than the PTFE group. The superiority of 2% HA hydrogels over 1.25% HA hydrogels and PTFE in maintaining tumour slice area was confirmed with another patient tumour (FIG. 6).

Figure 7:
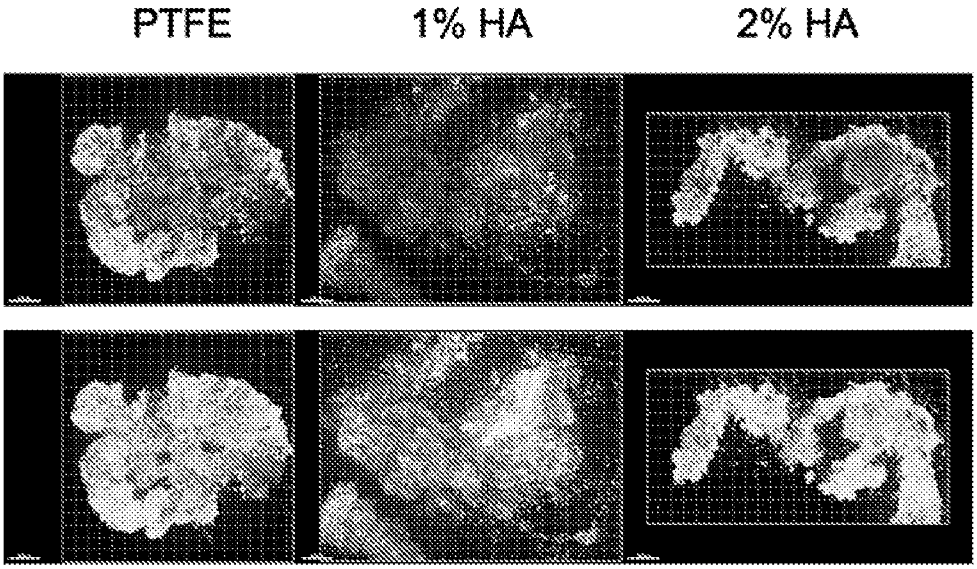
FIG. 7. Confocal images of tumour slices cultured on PTFE cell culture inserts, 1% HA hydrogels or 2% HA hydrogels, stained with Calcein-AM (green) for live cells and propidium iodide (red) for dead cells. Qualitatively, at Day 12, there were more dead cells (red) in 1% HA hydrogel. This illustrates the power of using tunable hydrogels for identifying optimal hydrogel parameters for maintaining tumour slice viability ex vivo.
Figure 8:
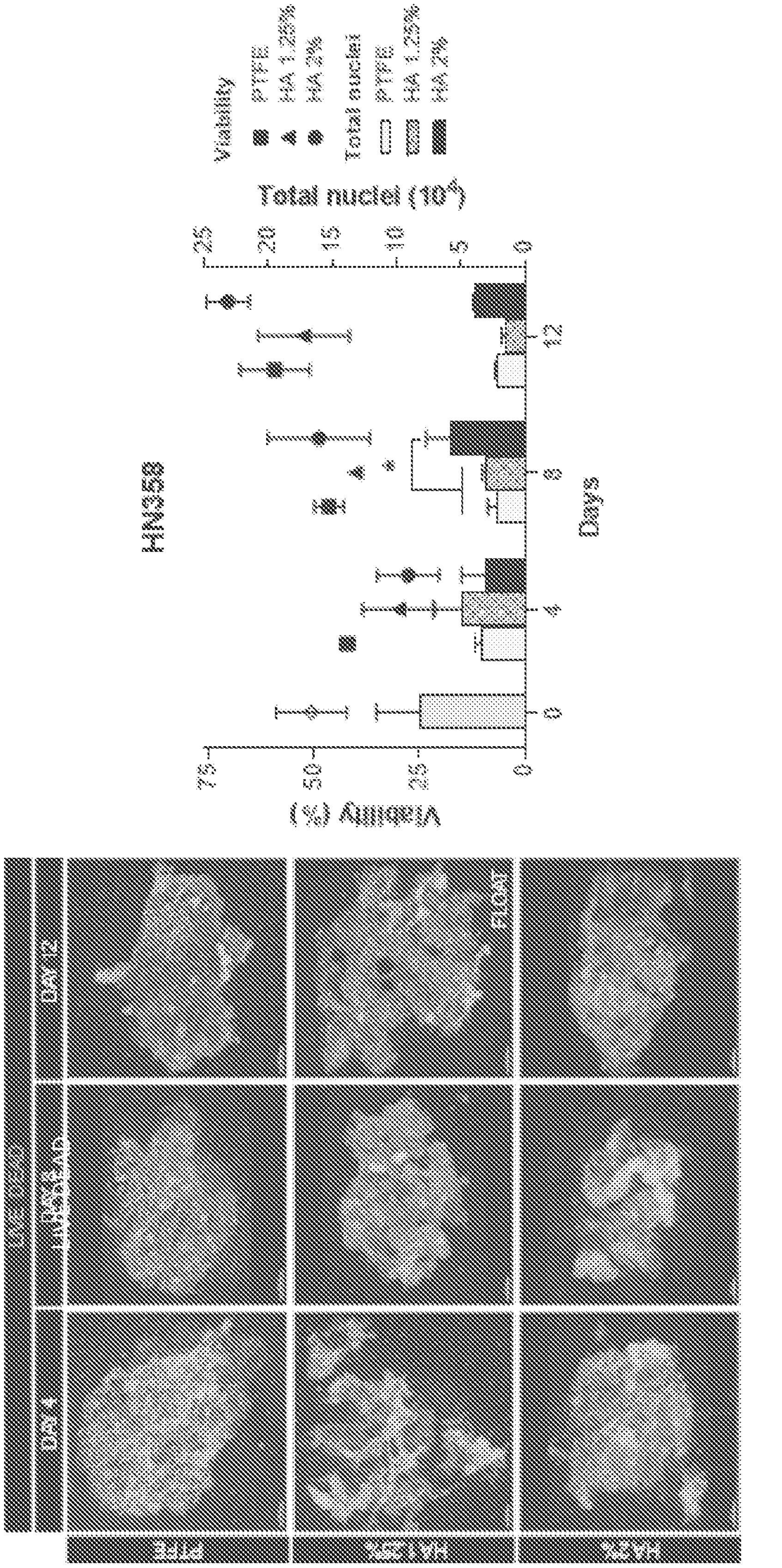
FIG. 8. Confocal images of tumour slices stained with Calcein-AM (green) for live cells and propidium iodide (red) for dead cells. Qualitatively, at Day 12, more dead cells (red) are observed for PTFE cell culture inserts and 1.25% HA hydrogel groups as compared to 2% HA hydrogels, suggesting 2% HA hydrogels best maintains tumour slice viability. Quantification of total nuclei count through images in shows 2% HA hydrogels (black bar graph) better preserves cell number in slices as compared to 1.25% HA hydrogels and PTFE. * represents $p<0.05$. Statistical significance in overall viability (dots in graph) was not reached between groups likely because normalization was done against total nuclei count (bars in graph) of differing numbers. Results suggest 2% HA hydrogel best preserves cell number compared to 1.25% HA hydrogels and PTFE cell culture inserts.
Figure 9:
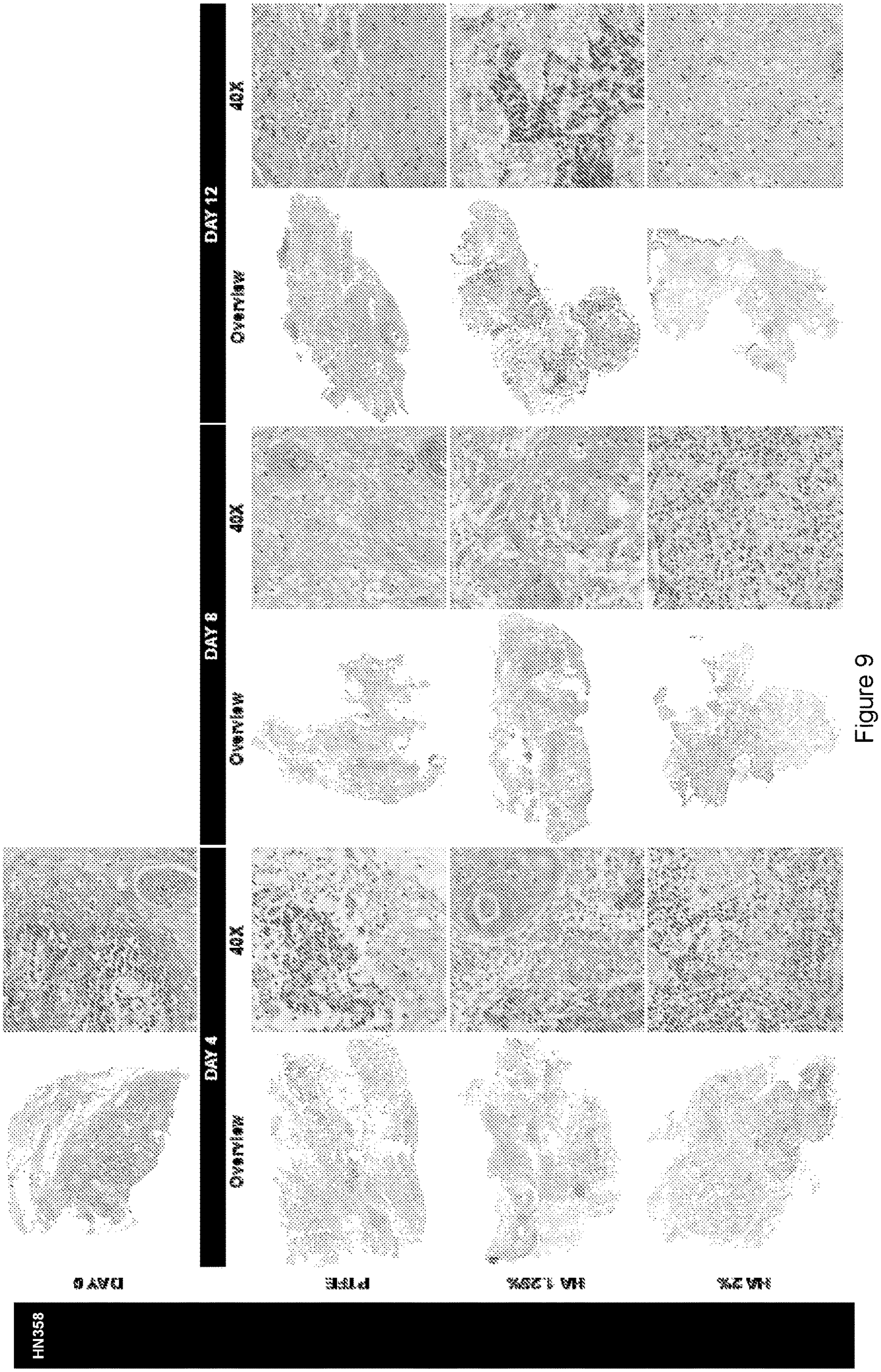
FIG. 9. Morphology of cultured tumour slices. Hematoxylin and eosin (H&E) staining was performed on the cultured tumour slices in both PTFE cell culture inserts and 2% HA hydrogel groups.

A qualitative evaluation of the effect of the stiffness of the hydrogel on slice viability is shown in FIG. 7, where we observed more dead cells in tumour slices cultured on 1% HA hydrogels were observed as compared to 2% HA hydrogels using live imaging. As further confirmation, live imaging of the tumour slices with Hoescht, Calcein AM and Propidium Iodide was performed, and this showed that the number of nuclei in slices on 2% HA hydrogels was significantly higher than that of 1.25%, even higher than PTFE (FIG. 8). These findings indicate that it is possible to optimize physical properties of the underlying matrix using hydrogels to identify conditions that better preserve tumour slices ex vivo than the use of PTFE cell culture inserts. Morphologically, loss of tumour architecture was observed in tumour slices cultured on 1.25% HA hydrogels, while tissue morphology was similarly preserved in 2% HA hydrogel and PTFE groups (FIG. 9). Accordingly, for subsequent studies, only 2% HA hydrogels were compared with PTFE. In sum, results here indicate the power of using tunable hydrogels for identifying important hydrogel parameters (such as stiffness) that govern tumour slice viability ex vivo.

2.2 HA Hydrogel Maintains Tumour Slice Viability and Proliferation

Figure 10:
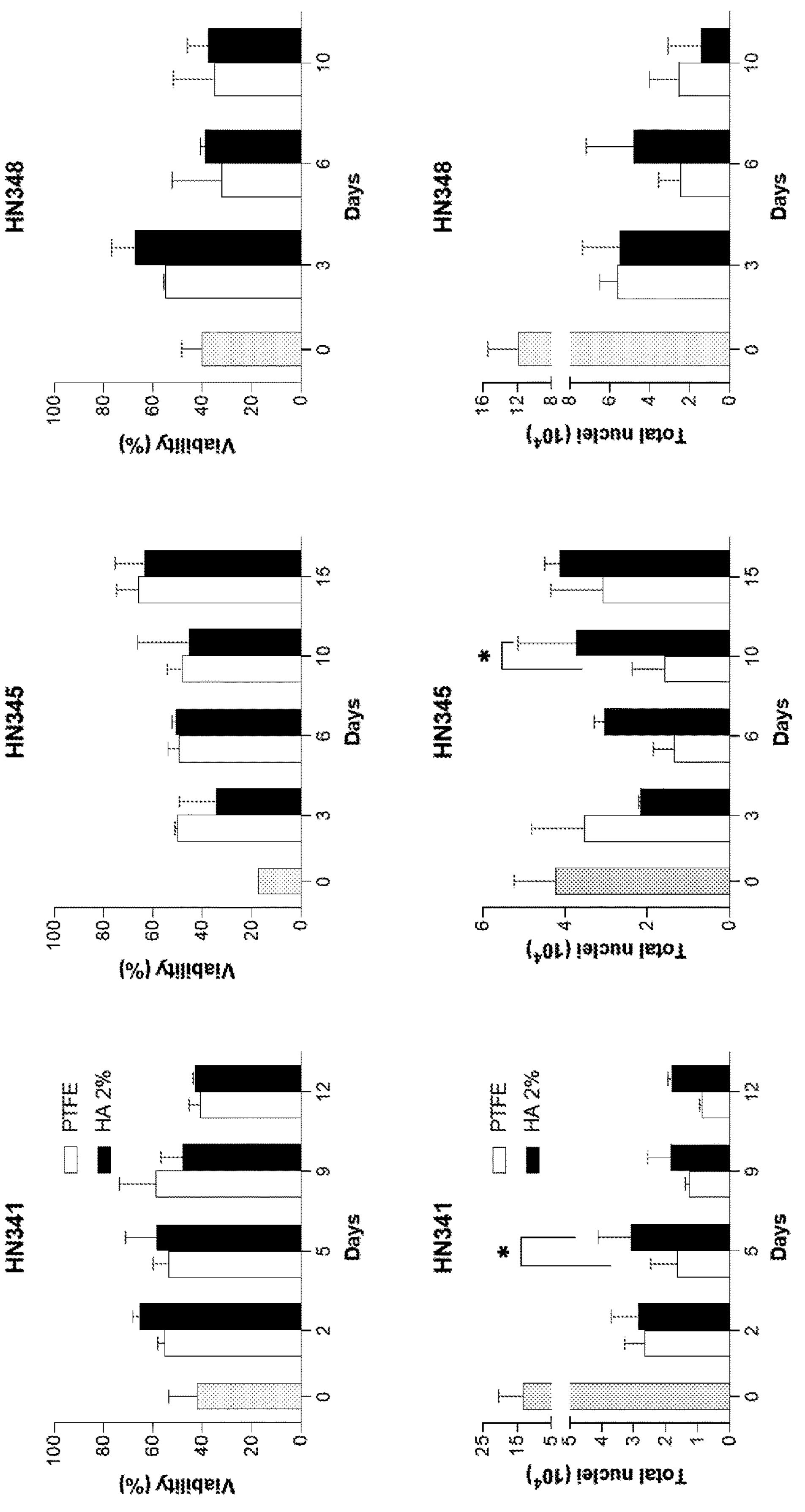
FIG. 10. HA hydrogels maintain cell viability and better preserve cell numbers than PTFE cell culture inserts for at least three patients. Quantification of viable cells (propidium iodide-negative, top row) and total nuclei count (bottom row) across different timepoint shows 2% HA hydrogels (black bar graph) better preserves cell number in slices as compared to PTFE. * represents $p<0.05$.
Figure 11:
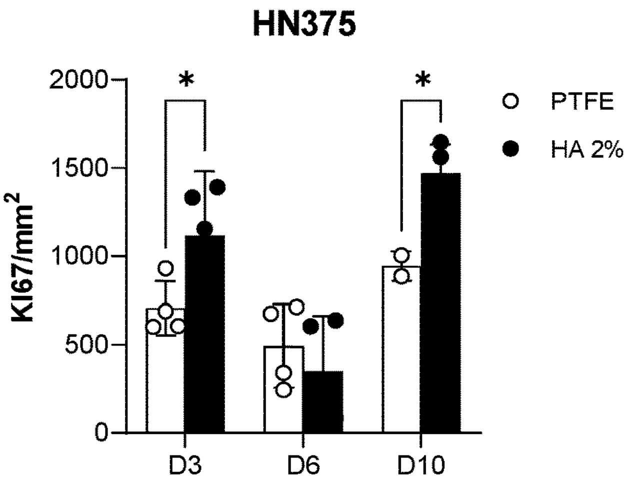
FIG. 11. HA hydrogels better preserve cell proliferation compared to PTFE cell culture inserts. AI-based algorithm was used to quantify IHC images. Quantification of Ki67-positive cells (Ki67/$mm^2$) by immunohistochemistry shows higher proportion of Ki-67-positive cells in slices cultured on 2% HA hydrogels compared to PTFE on Day 10. * represents $p<0.1$. Results suggest 2% HA hydrogels better supports cell proliferation in slice cultures as compared to PTFE.

Beyond tissue volume and architecture, it was next investigated whether the tunable hydrogels were also able to maintain tumour slice viability and proliferation. Subjecting tumour slices to live-labeling for live and dead cells, the total cell number as well as viability were quantified (FIG. 10). Comparing tumour slices cultured on 2% HA hydrogels to PTFE, there was no statistically significant differences between the two groups. Tumour slice viability was maintained in both systems for at least 2 weeks in culture at above 60% for over 4 patients. Furthermore, the percentage of Ki67-positive cells was higher in the HA hydrogel compared to PTFE (FIG. 11), suggesting that HA hydrogels are conducive for the maintenance of tumour slice viability and proliferation, and in some cases, even better than PTFE.

Figure 12:
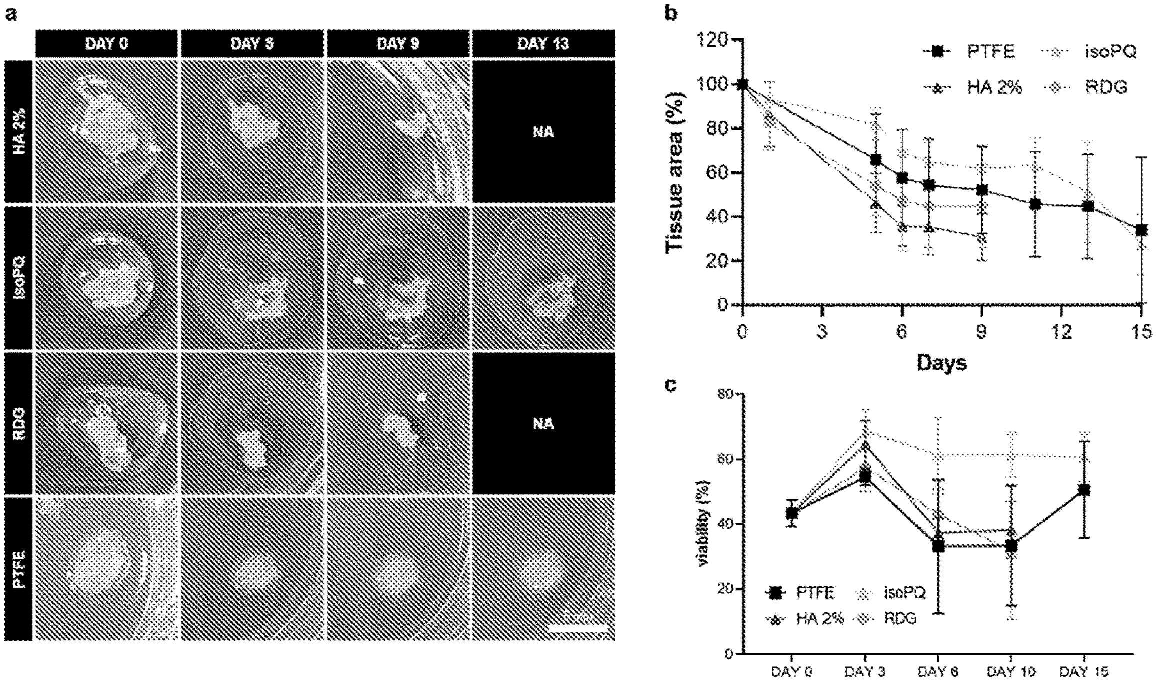
FIG. 12. To investigate parameters important for maintaining tumour slice cultures such as hydrogel degradability and focal adhesion, non-degradable crosslinker (isoPQ) and scrambled integrin-binding peptide sequence (RDG) were used respectively. IsoPQ hydrogels have limited degradability as compared to PQ hydrogels. Gross images (a) showed that PQ-hydrogels (2% HA and RDG) degraded over time, which correlated with (b) more rapid shrinking of the tumour slice measured by tissue slice area and (c) lower tumour slice viability compared to isoPQ hydrogels. Results suggest that limited/no degradation is a necessary feature of hydrogels for maintaining tumour slices.
Figure 13:
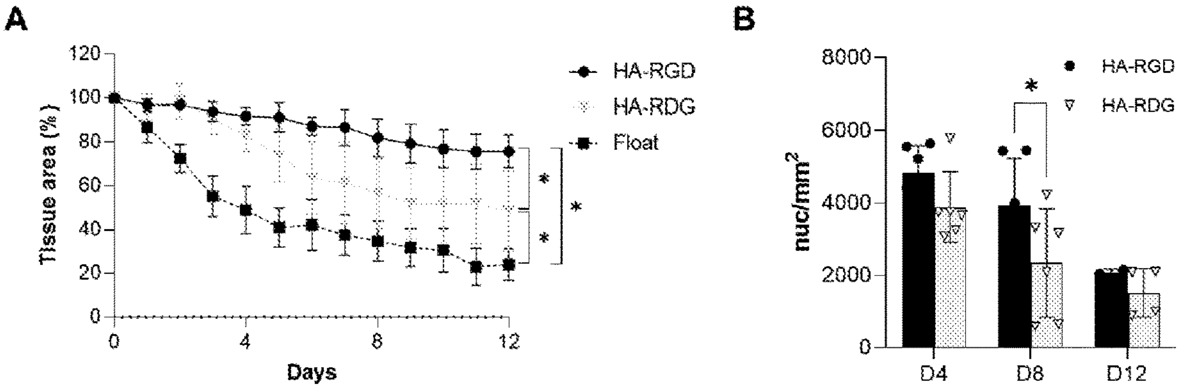
FIG. 13. Tunable hydrogels allow for independent investigations into parameters that influence tumour slice viability. Results suggest that provision of integrin-binding sites is necessary for preserving tumour slice area and cell number. (A) Tumour slices were cultured on HA hydrogels that presented RGD for integrin-binding versus the scrambled version (RDG), which does not support integrin-binding. Quantification of tumour slice area (% of Day 0) over time shows that HA-RGD hydrogels best preserves tumour slice area, compared to HA-RDG and floating groups. In the floating group, slices were cultured without any underlying substrate. Data highlights the importance of slice adhesion to the underlying substrate and how hydrogels can serve as a tunable matrix to provide this support. * represents $p<0.05$. (B) Quantification of total nuclei count by H&E staining (nuc/$mm^2$); results suggest that tumour slice cell number is better preserved in the presence of integrin-binding sites (RGD), which enable slice to have adhered to the underlying hydrogel. * represents $p<0.05$.

2.3 Tuning Hydrogel Parameters Enable Identification of Important Parameters Governing Tumour Slice Viability Beyond hydrogel stiffness, it was further investigated whether tuning/modulating hydrogel parameters such as adhesivity and degradability would contribute to improved viability of tumour slices. Results are shown in FIGS. 12 and 13. First, it was found that impeding hydrogel degradation using non-degradable peptide sequences (isoPQ) better maintained tissue slice area (FIGS. 12A and B) and enhanced tumour slice viability (FIG. 12C) as compared to degradable hydrogels (HA 2%) and PTFE. Second, focusing on the Arg-Gly-Asp (RGD) sequence found in many ECM components (e.g. fibronectin), HNSCC tumour slices were cultured on hydrogels with RGD or the scrambled version, RDG. It was found that RGD is necessary for preserving tumour slice area and cell number, presumably for enabling the tumour slice to remain adhered onto the hydrogel (FIGS. 13A and 13B). These results highlight the importance of leveraging tunable hydrogels for determining important hydrogel parameters that enhance tumour slice viability ex vivo.

Figure 14:
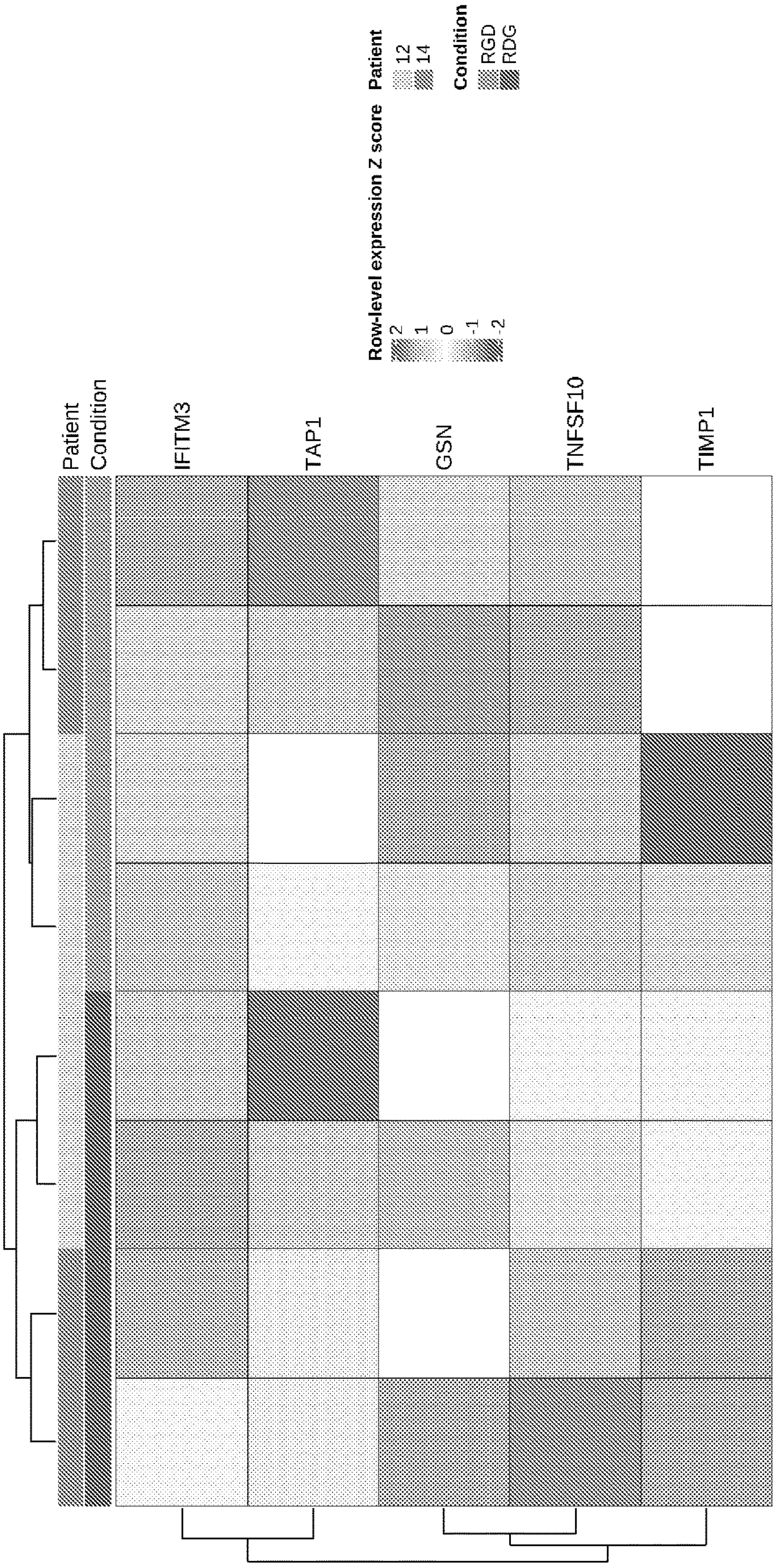
FIG. 14. Heatmap comparing apoptosis-related genes in tumour slices cultured on HA-RGD or HA-RDG, for two patients—Patient 12 (HN382) and Patient 14 (HN386). Higher expression levels of these pro-apoptotic genes are observed in tumour slices cultured on HA-RDG, suggesting importance of RGD in promoting cell survival in the hydrogel-cultured tumour slice.
Figure 15:
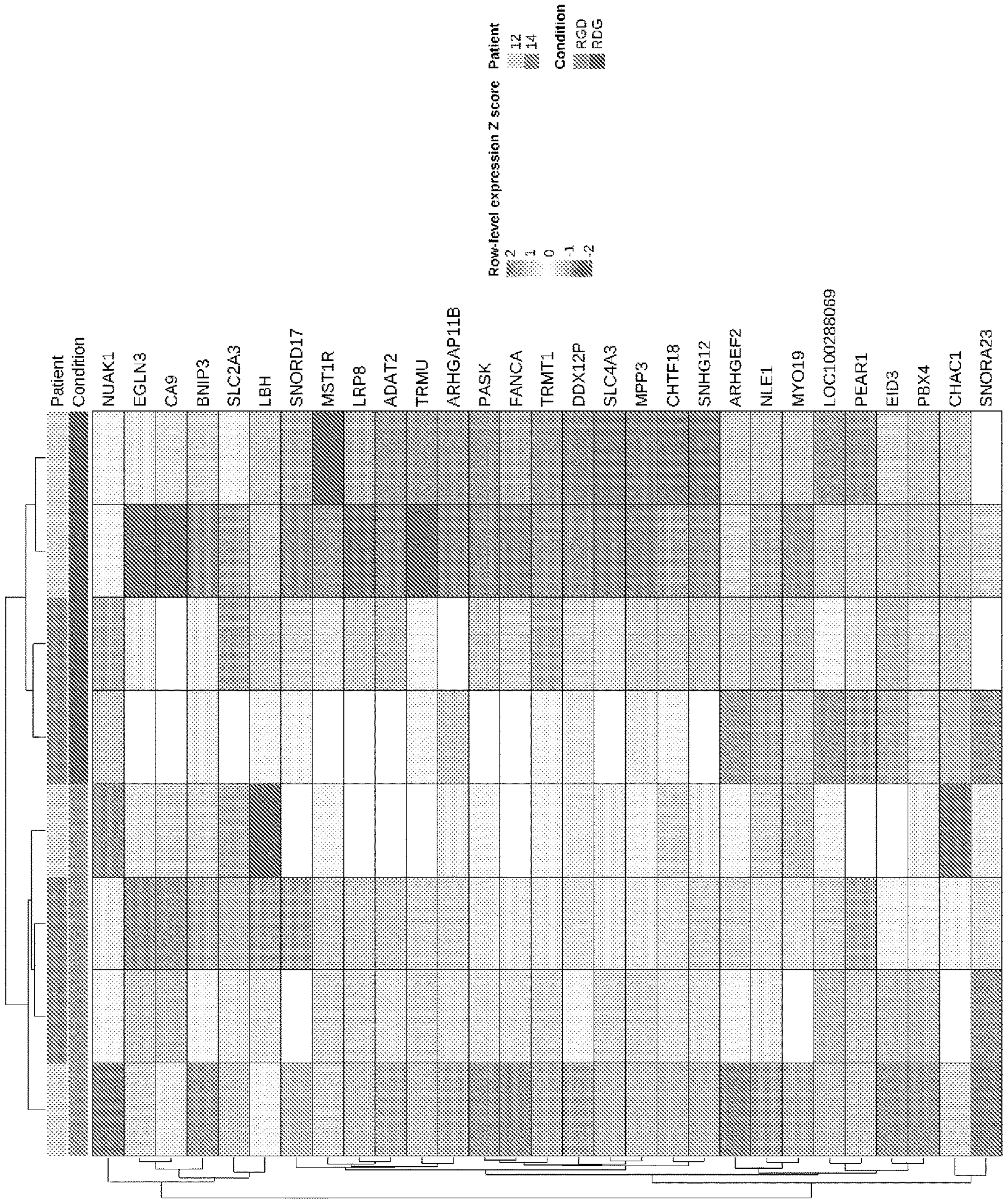
FIG. 15. Heatmap of YAP target genes in tumour slices cultured on HA-RGD or HA-RDG, for two patients—Patient 12 (HN382) and Patient 14 (HN386). Higher expression levels of these YAP-target genes are observed in tumour slices cultured on HA-RGD as compared to HA-RDG.
Figure 16:
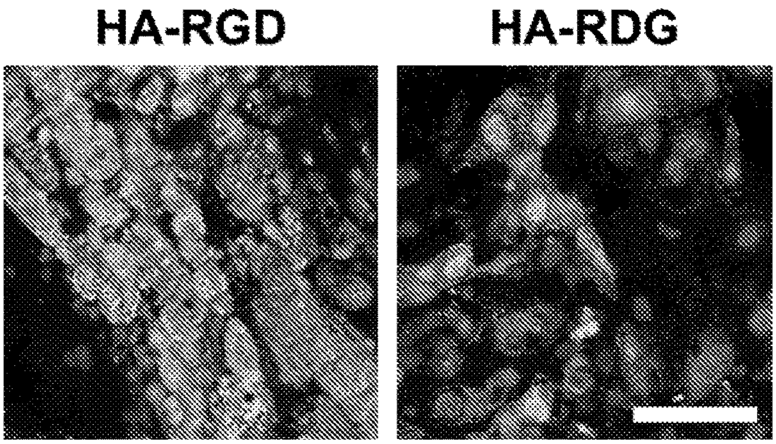
FIG. 16. Immunofluorescence staining for active YAP in tumour slices cultured on HA-RGD vs HA-RDG. Higher YAP activity is observed in cells within tumour slices on HA-RGD compared to those on HA-RDG. Scale bar: 50 μm.

To further investigate whether the provision of integrin-binding affects the phenotype of cells within the tumour slice, tumour slices cultured on HA-RGD or HA-RDG were subjected to RNA sequencing. As shown in FIG. 14, higher expression levels of genes that are pro-apoptosis in the HA-RDG-cultured tumour slices were observed compared to the HA-RGD-cultured tumour slices, suggesting that the presentation of the RGD peptide enables recapitulation of ECM-integrin interactions necessary to prevent cell death. Given how Hippo effectors YAP/TAZ act as mechanosensors by sensing modifications in the extracellular matrix and mechanics through integrins, we asked whether YAP activity was altered between the HA-RGD vs HA-RDG condition. As shown in FIG. 15, the upregulation of many genes associated with YAP activation in tumour slices that were cultured on HA-RGD was observed, suggesting that HA-RGD promotes integrin-mediated YAP activation. This finding was validated by performing immunofluorescence staining for YAP in the tumour slices and confirmed the presence of more YAP-active cells in tumour slices cultured on HA-RGD, as compared to HA-RDG (FIG. 16). In sum, our results here demonstrate the utility of semi-synthetic/synthetic hydrogels for tuning and investigating the effects of different biochemical and biophysical matrix parameters on tumour slice culture.

Figure 17:
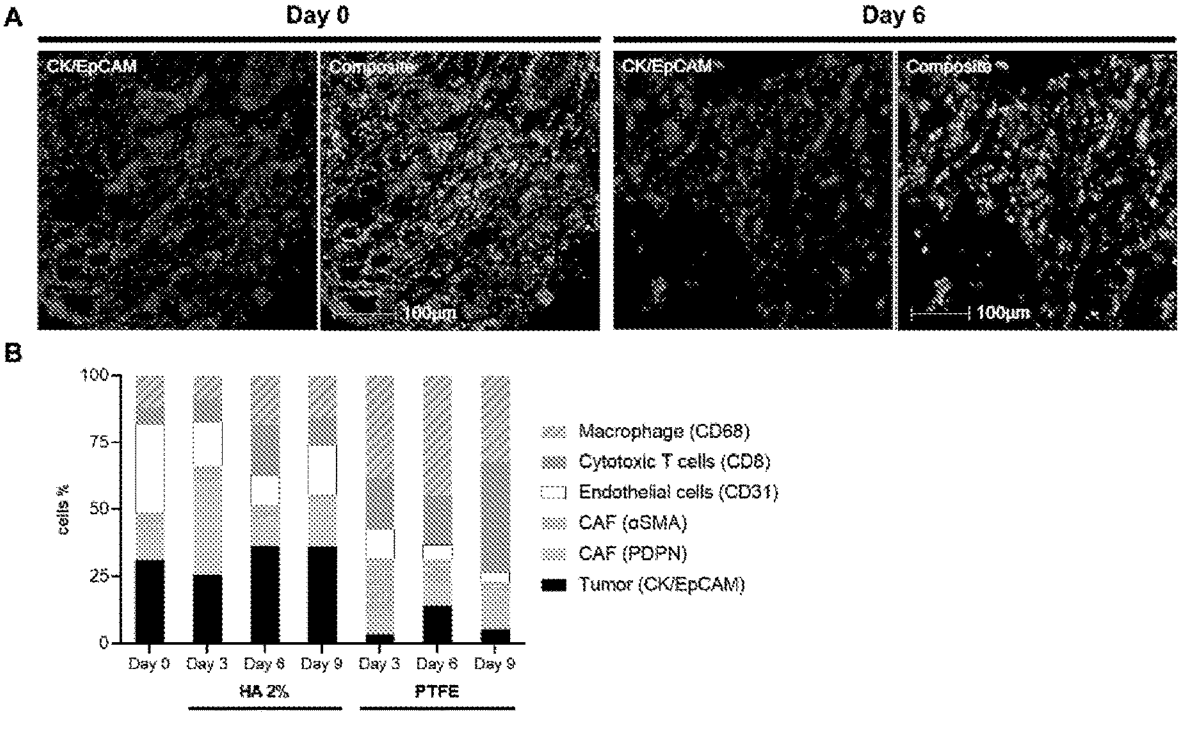
FIG. 17. HA hydrogels preserve the original tumour composition of cultured slices. Multiplex immunofluorescence was performed on slices (cultured on 2% HA hydrogels or PTFE cell culture inserts) at Day 0 (original tumour) and after 3, 6 or 9 days in culture. (A) Confocal images of tumour slice sections stained with DAPI (blue), and with antibodies against CD8 (green), PDPN (orange), CD68 (yellow), CD31 (magenta), SMA (cyan), CK/EpCAM (red). Magnification, 200×. (B) Quantification of the proportion of different cancer and stromal cell populations across 9 days in culture: tumour (cancer cells), cancer-associated fibroblasts (CAF_PDPN+ and CAF_α-SMA+), endothelial cells (EC), cytotoxic T-cells (CTL), macrophages (MØ). Results show HA hydrogels preserve major cancer and stromal cell populations, and HA hydrogels better preserve the proportion of cancer and major stromal populations as compared to PTFE cell culture inserts.
Figure 18:
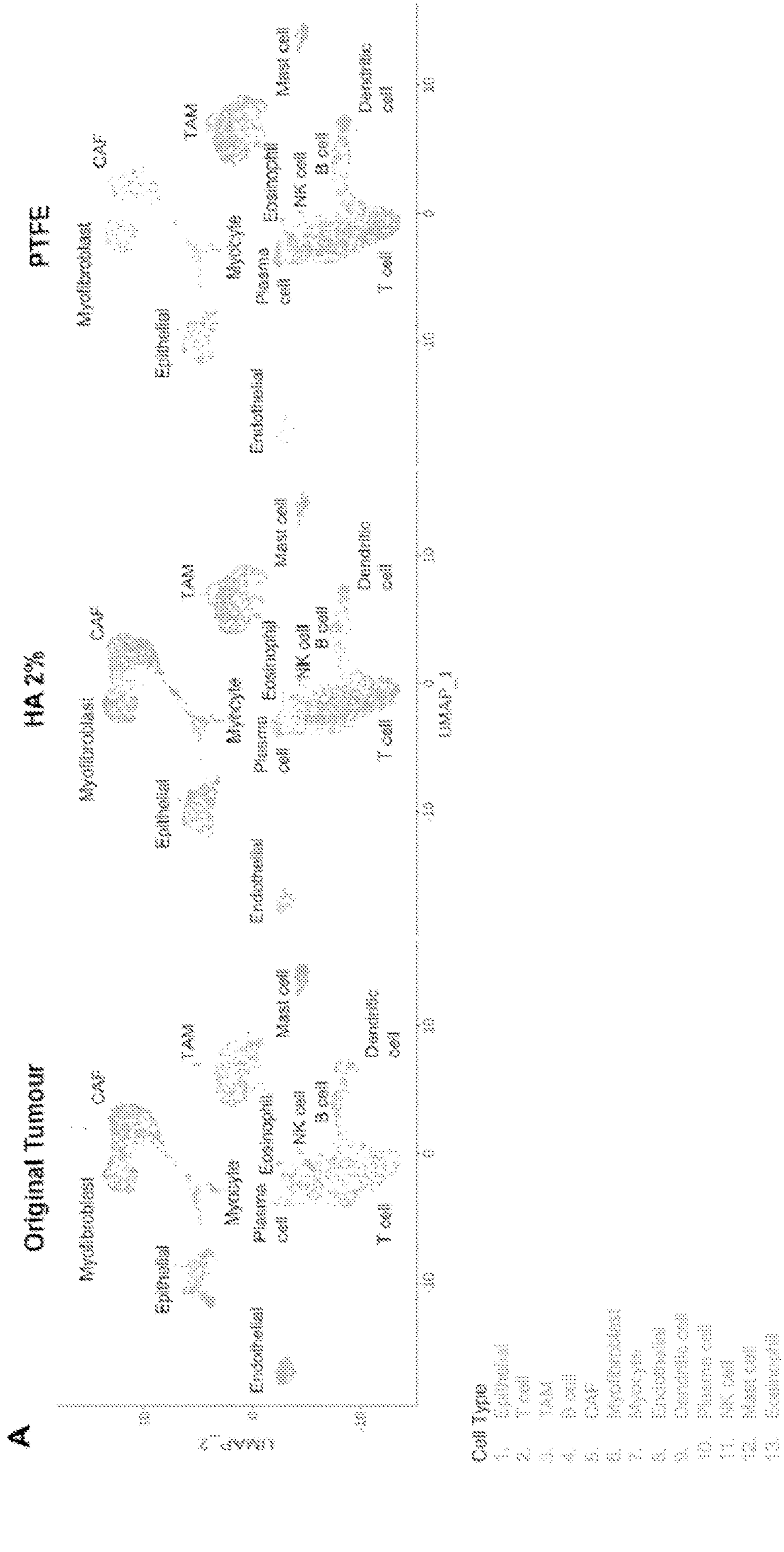
FIG. 18. Single cell-RNA sequencing for Patient 10 (HN377) reveals HA hydrogels better maintain original tumour composition and heterogeneity in cancer-associated fibroblasts (CAFs) than PTFE. (A) UMAP plots of original tumour at Day 0 (left), slices cultured on HA hydrogel (HA 2%, middle), and PTFE cell culture inserts (right) at Day 7. Consistent with results from multiplex immunofluorescence (FIG. 17), results show HA hydrogel preserves all major cell types in the original tumour. Specifically, while HA hydrogels are able to preserve CAFs (green cluster) and endothelial cells at Day 7, we observe the loss of these populations in the PTFE group. (B) Quantification of the proportion of various cancer and stromal populations shows that HA hydrogels better maintains the original proportion of epithelial cancer (#1), T-cells (#2), tumour-associated macrophages (TAMs) (#3), CAFs (#5), myofibroblasts (#6), endothelial cells (#8), dendritic cells (#9) as compared to PTFE. (C) UMAP plots of Epithelial (cancer), CAF, T-cell and TAM subpopulations of original tumour at Day 0 (left column), and slices cultured on HA hydrogel (middle column) and PTFE (right column) at Day 7. Results show that HA hydrogels preserve cancer, CAF, T-cell and TAM heterogeneity (presence of subpopulations). The presence of important T-cell subsets such as cytotoxic CD8+ T-cells, regulatory T-cells (Treg) and CD4+ T-cells in slices cultured on HA hydrogels is especially encouraging since these are important mediators of response and resistance to ICI. Additionally, we observe presence of Ki-67-positive cancer cells in HA hydrogels, indicating that HA hydrogels are able to preserve cancer proliferative status, important for using the model to evaluate chemotherapeutics that target actively dividing cells. Importantly, HA hydrogels are able to preserve CAF subpopulations i.e. myofibroblast CAFs (myCAFs) and inflammatory CAFs (iCAFs), but not PTFE. This is a critical difference between HA hydrogels and PTFE cell culture inserts as CAF subsets are highly investigated now as mediators of ICI response and resistance.
Figure 18:
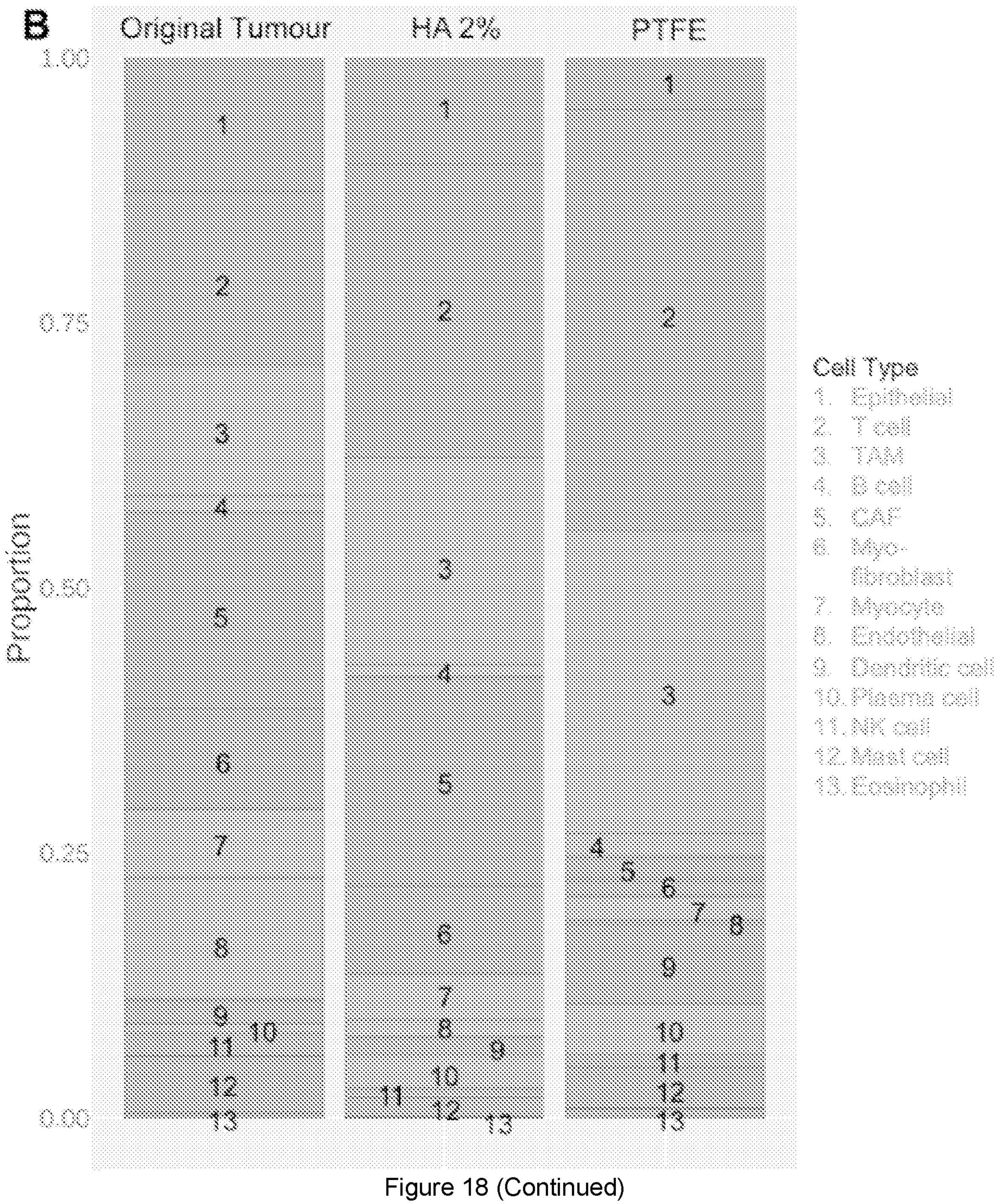
Figure 18:
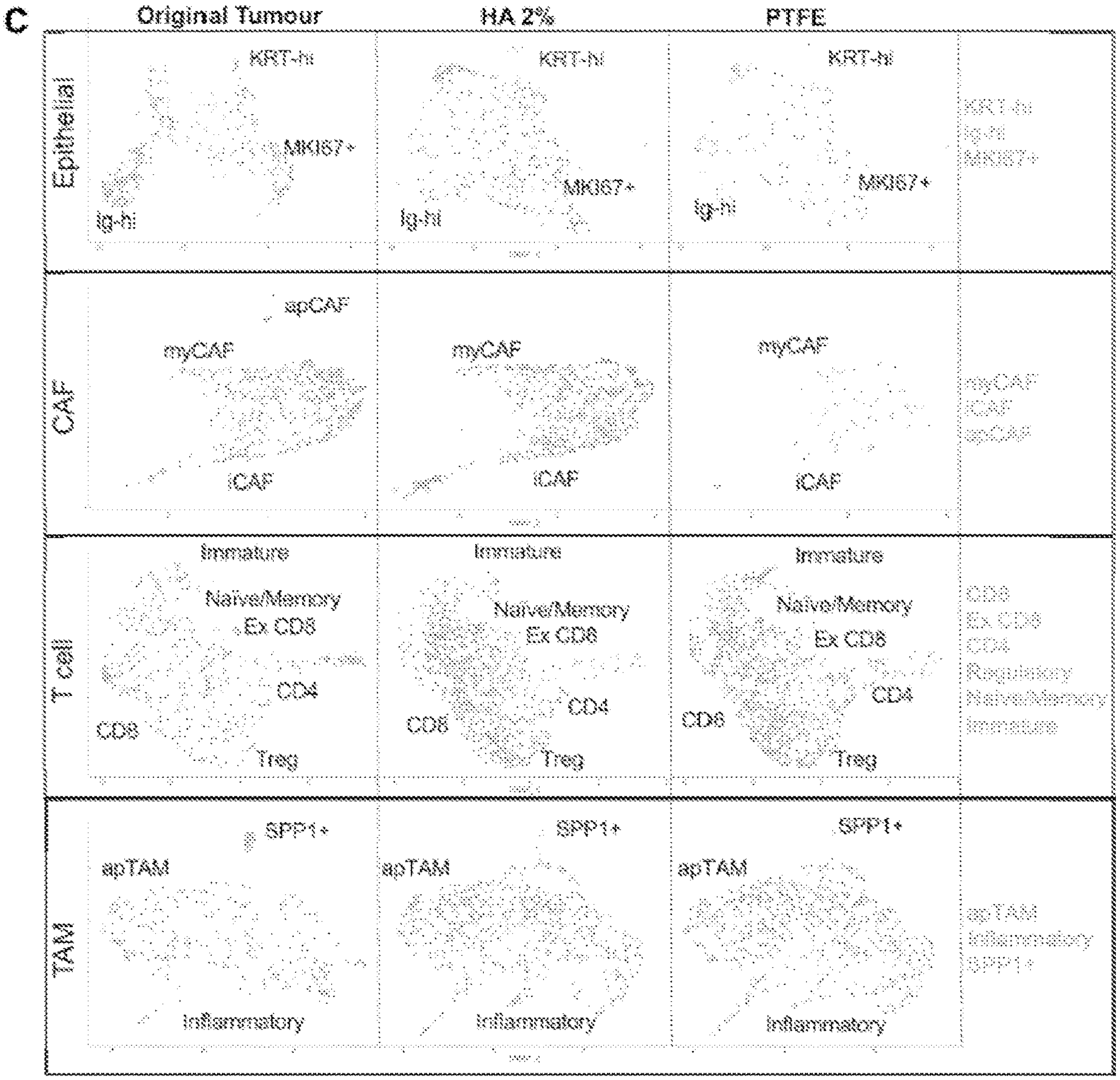
Figure 19:
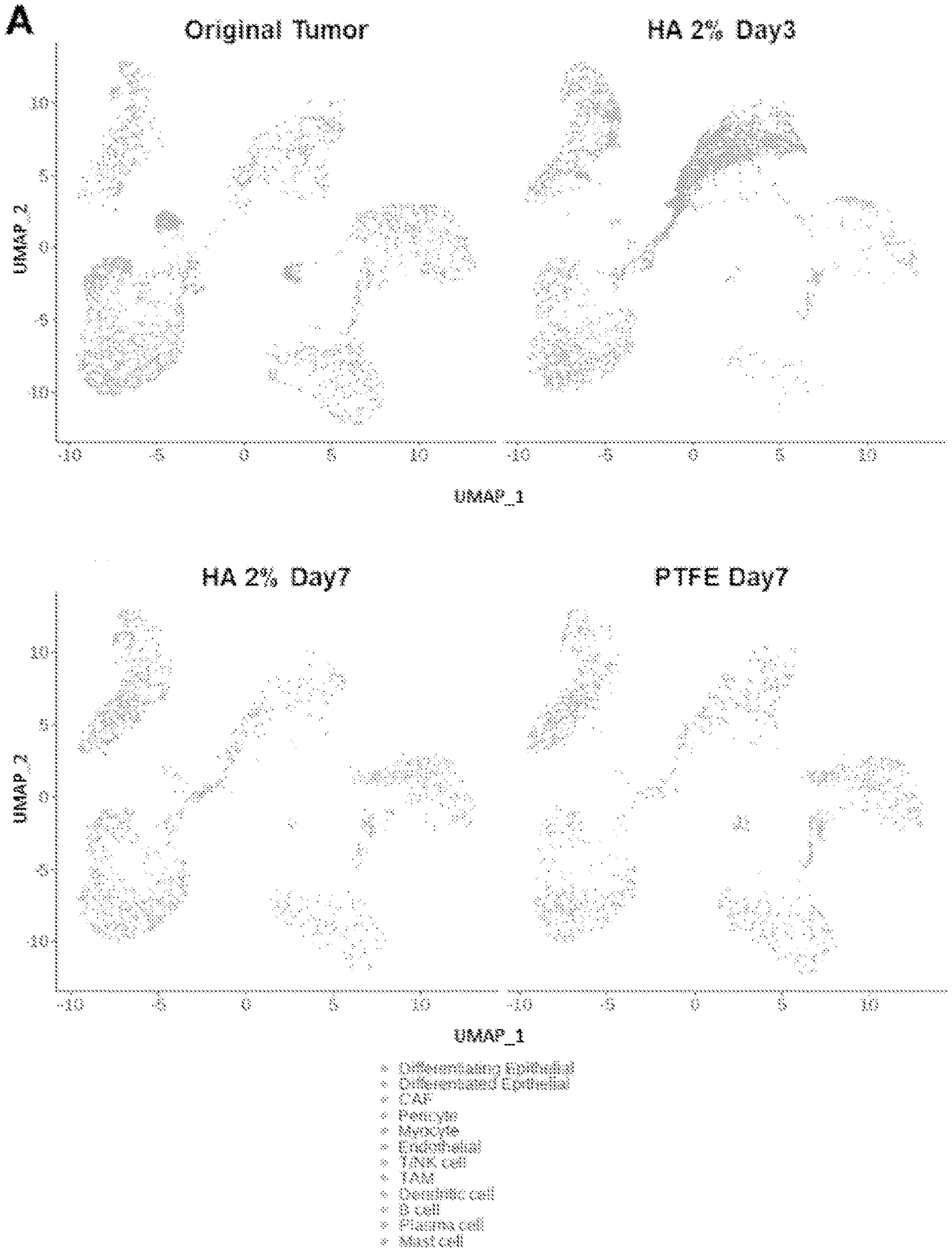
FIG. 19. Single-cell RNA sequencing of Patient 13 (HN385) HNSCC tumour and corresponding tumour slices also shows HA hydrogels maintain original tumour composition for at least 7 days of culture, consistent with findings from Patient 10 (HN377) in FIG. 18.
Figure 19:
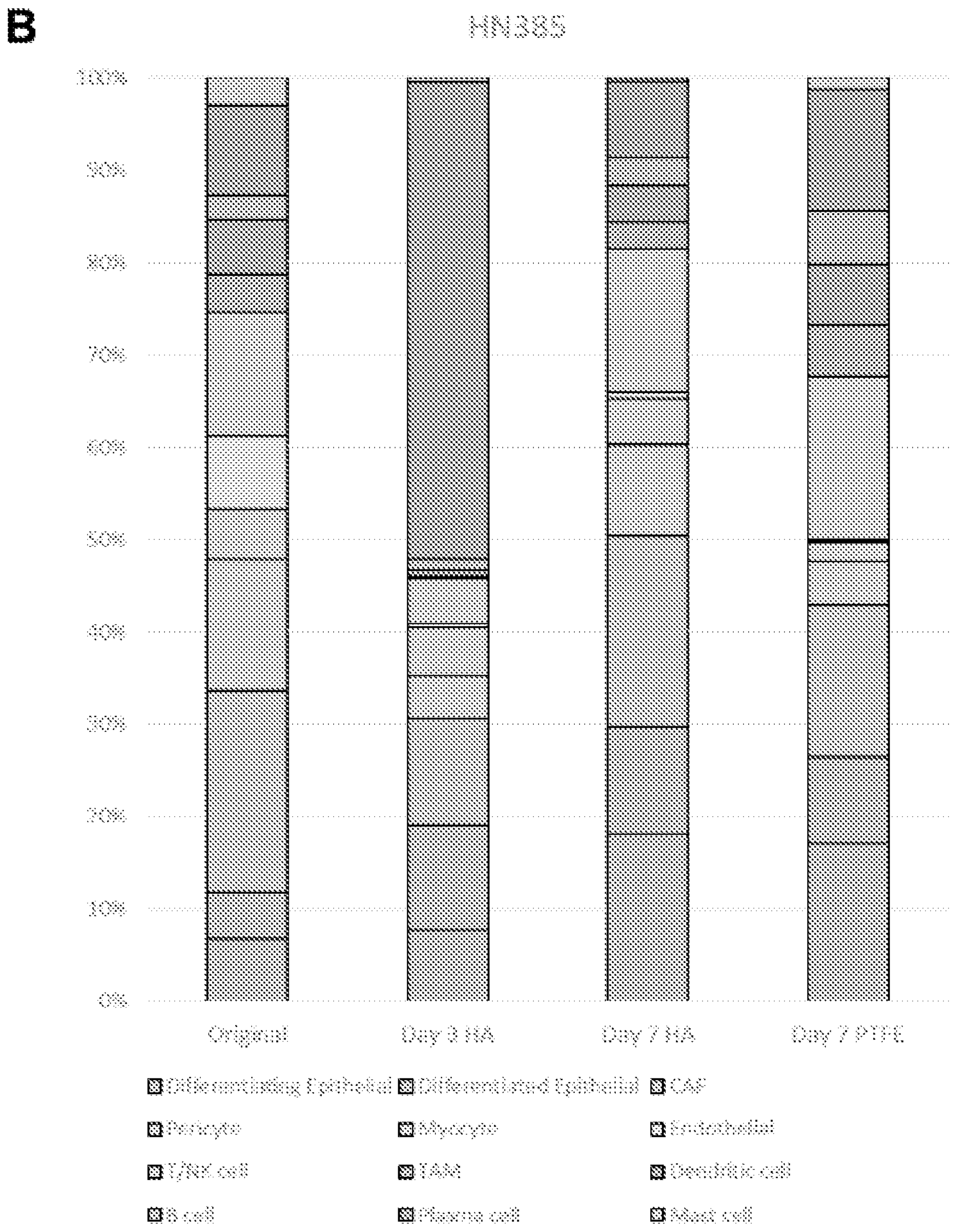
Figure 20:
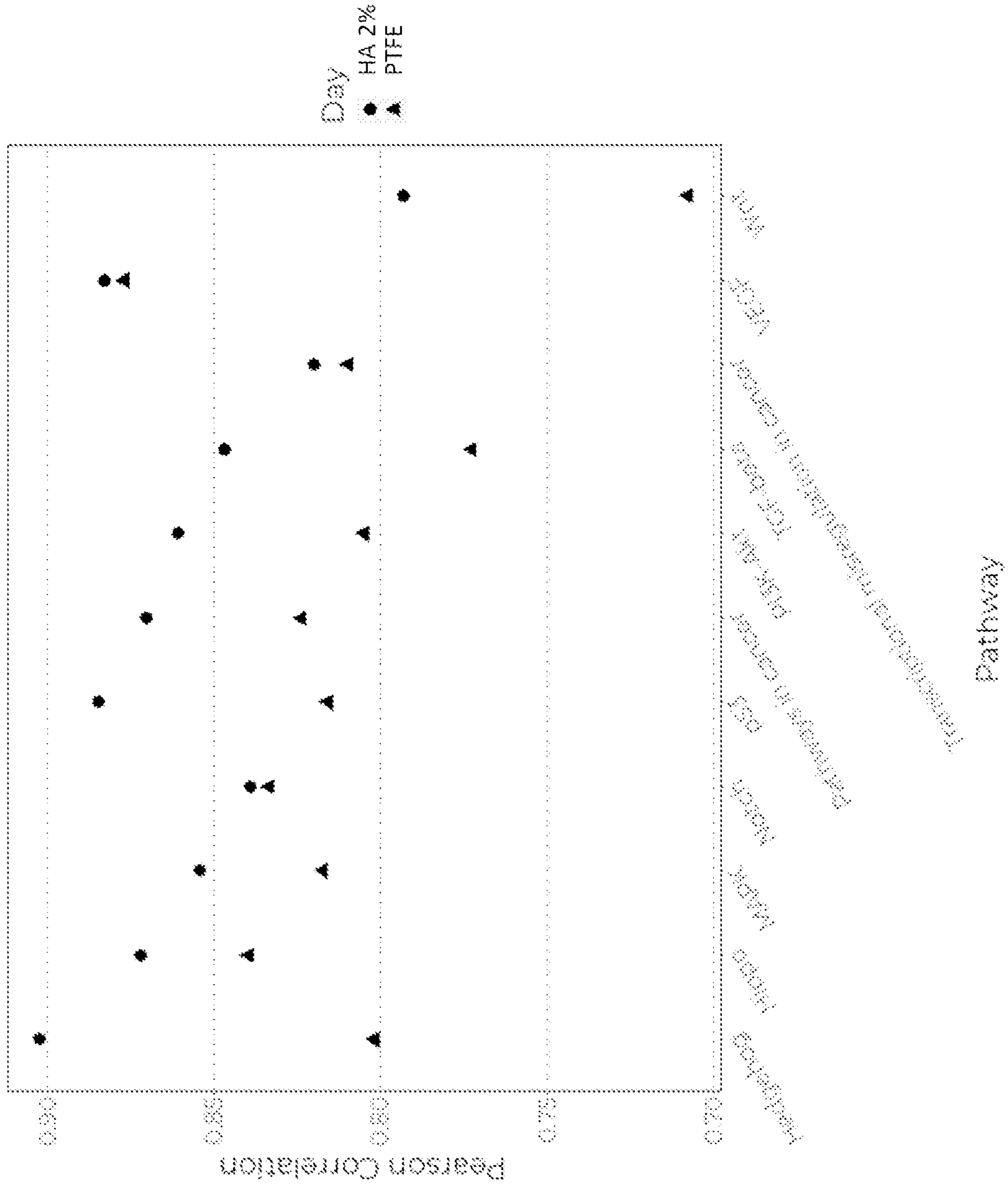
FIG. 20. scRNAseq reveals HA hydrogels better preserve gene expression profile of cancer cells compared to PTFE cell culture inserts. Pearson correlation coefficients (y-axis) for HA hydrogel (HA 2%) and original tumour, versus PTFE and original tumour, for cancer-related pathways. Pearson correlation coefficient measures the extent to which the expression of genes in these cancer-related pathways in cancer cells is similar between HA hydrogels (or PTFE) to the original tumour. The Pearson correlation coefficient is all above 0.8 for HA and PTFE, suggesting strong correlation of cancer gene expression profiles for both systems to original tumour. However, we observe higher correlation in the HA hydrogel group compared to PTFE for most of these cancer-related signaling pathways, indicating that HA hydrogels better maintain the gene expression profile of cancer cells in important cancer-related pathways compared to PTFE.

2.4 Engineered Tumour Slices Better Preserve Original Tumour Composition as Compared to PTFE Multiplex immunofluorescence was used to deeply characterize the composition of the cultured tumour slices. As shown in FIG. 17, using key markers for cancer, CAFs, endothelial cells, macrophages and cytotoxic T-cells, preservation of all key cancer and stromal cell types in our engineered tumour slice cultures was observed. It was also observed that HA hydrogels better preserve the cancer and stromal populations as compared to PTFE. Strikingly and corroborating multiplex immunofluorescence findings, when tumour slices cultured in the two systems were subjected to single-cell RNA sequencing, enhanced preservation of most cell types (cancer, T-cells, macrophages, endothelial, CAFs, dendritic cells etc.) in tumour slices that were cultured on HA hydrogels was observed compared to slices cultured on PTFE (FIGS. 18A and B). Notably, the myofibroblasts, CAFs and endothelial populations were lost in PTFE cultures, but not in the HA hydrogels. Furthermore, it was found that at the subpopulation level, while various T-cell and macrophage subpopulations were preserved in both HA hydrogel and PTFE cultures, there was a clear loss of CAF subpopulations (myofibroblastic CAFs and inflammatory CAFs) (FIG. 18C). The presence of important T-cell subsets such as cytotoxic CD8+ T-cells, regulatory T-cells (Treg) and CD4+ T-cells in slices cultured on HA hydrogels is especially encouraging since these are important mediators of response and resistance to ICI. The presence of Ki-67-positive cancer cells was also observed in HA hydrogels, indicating that HA hydrogels are able to preserve cancer proliferative status, an important parameter to maintain in order to use the model for evaluating chemotherapeutics that target actively dividing cells. We confirmed that HA hydrogels are able to preserve major cell populations by performing single-cell RNA sequencing analysis of tumour slice cultures generated from another patient (FIG. 19). Together, these results suggest that HA hydrogels provide a more in vivo-like environment that enables maintenance of tumour composition as compared to PTFE, even at 7 days in culture. Lastly, given the importance of preserving the molecular profile of cancer cells in slice cultures, we compared the expression of genes in key cancer-related pathways within cancer cells (including MAPK, Wnt and PI3-Akt) in the slice cultures on HA hydrogel vs PTFE. As shown in FIG. 20, greater correlation in the expression level of genes in slices that were cultured on HA hydrogels was observed, suggesting that HA hydrogels are better able to preserve the gene expression profile of cancer cells as compared to PTFE.

2.5 Engineered Tumour Slices Reflect Inter-Patient Heterogeneity in Response to Immune Checkpoint Blockade Since the engineered tumour slice cultures cultured using hydrogels are able to preserve the entire TME for at least 7 days in culture, including key cell types such as CAFs and the various immune cell populations, an investigation into whether these slice cultures could be used for evaluating the efficacy of immune checkpoint inhibitors was conducted. The plan was to determine whether anti-PD1 antibodies would be able to effectively penetrate and bind to PD1 on CD8+ T-cells, since the tissue itself may present as a barrier for antibody diffusion. Using flow cytometry, it was shown that the expression of PD1 on CD8+ T-cells in engineered tumour slices that were treated with pembrolizumab was almost completely blocked (FIGS. 21A and B), indicating that these slice cultures would be amenable for the evaluation of antibody-based drugs such as pembrolizumab. Additionally, for one patient in (FIG. 21A), a decrease in granzyme B over time was observed, suggesting degranulation has occurred.

Figure 21:
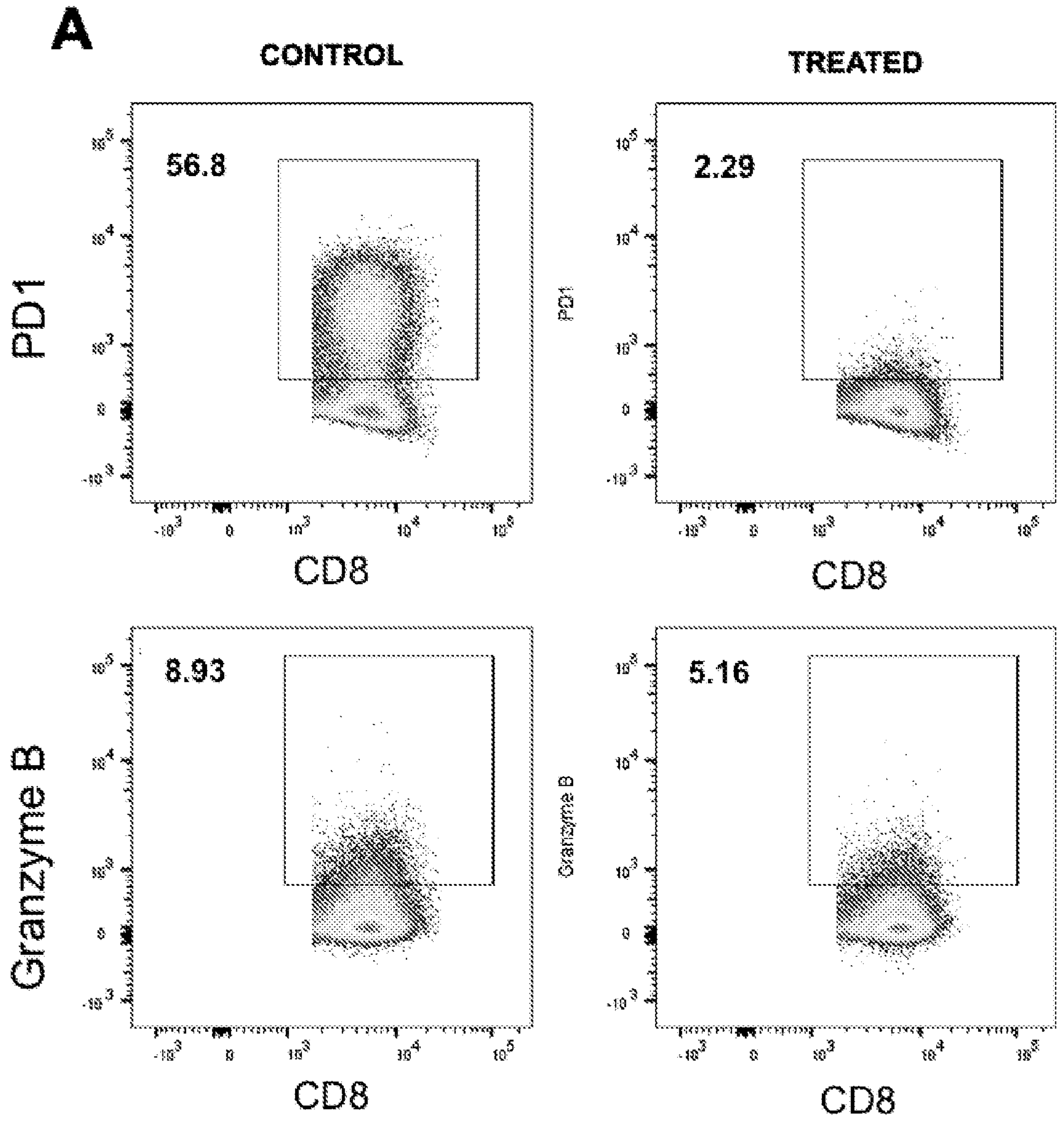
FIG. 21. Response of engineered HNSCC patient tumour slices to HNSCC standard-of-care drugs, pembrolizumab (Pem, anti-PD-1) and cisplatin (Cis). (A) Patient 6 (HN358): Flow histogram shows reduction of PD-1 expression in CD8+ cytotoxic T-cells (56.8% vs 2.3%), indicating that pembrolizumab can effectively block PD-1 within the tumour slices. Compared to control, a slight decrease in granzyme B expression in CD8+ cells was also observed (8.9% vs 5.2%), suggesting degranulation has occurred. (B) Patient 7 (HN359): Flow histogram shows reduction of PD-1 expression in CD8+ cytotoxic T-cells (37.5% vs 0.2%), again indicating that pembrolizumab can effectively block PD-1 within the tumour slices. Here, contrasting with Patient 6 (HN358), a slight increase in granzyme B expression in CD8+ cells was observed. (C) Tumour slices treated with cisplatin or control can be processed for dual immunohistochemistry to probe for pan-cytokeratin (brown, for cancer) and cleaved caspase-3 (red, for apoptotic cells). (D) Tumour slices can also be processed for dual immunofluorescence to stain for pan-cytokeratin (red), cleaved caspase-3 (green) and DAPI (blue, nuclei). (E) Quantification of cancer cell kill is achieved by leveraging automated software to detect pan-cytokeratin+ and cleaved caspase-3+ cells by dual IHC or IF. For Patient 6 (HN358), ~25% cleaved caspase-3 positivity (apoptotic) was detected in cancer cells within pembrolizumab-treated slices versus ~11% in controls at Day 2. ~12% apoptotic cancer cells was detected in cisplatin-treated slices versus ~5% in controls. (F) Quantification was performed the same for Patient 7 (HN359) pembrolizumab-treated tumour slices. Unlike Patient 6 (HN358), no enhanced tumour kill was observed in drug-treated slices.
Figure 21:
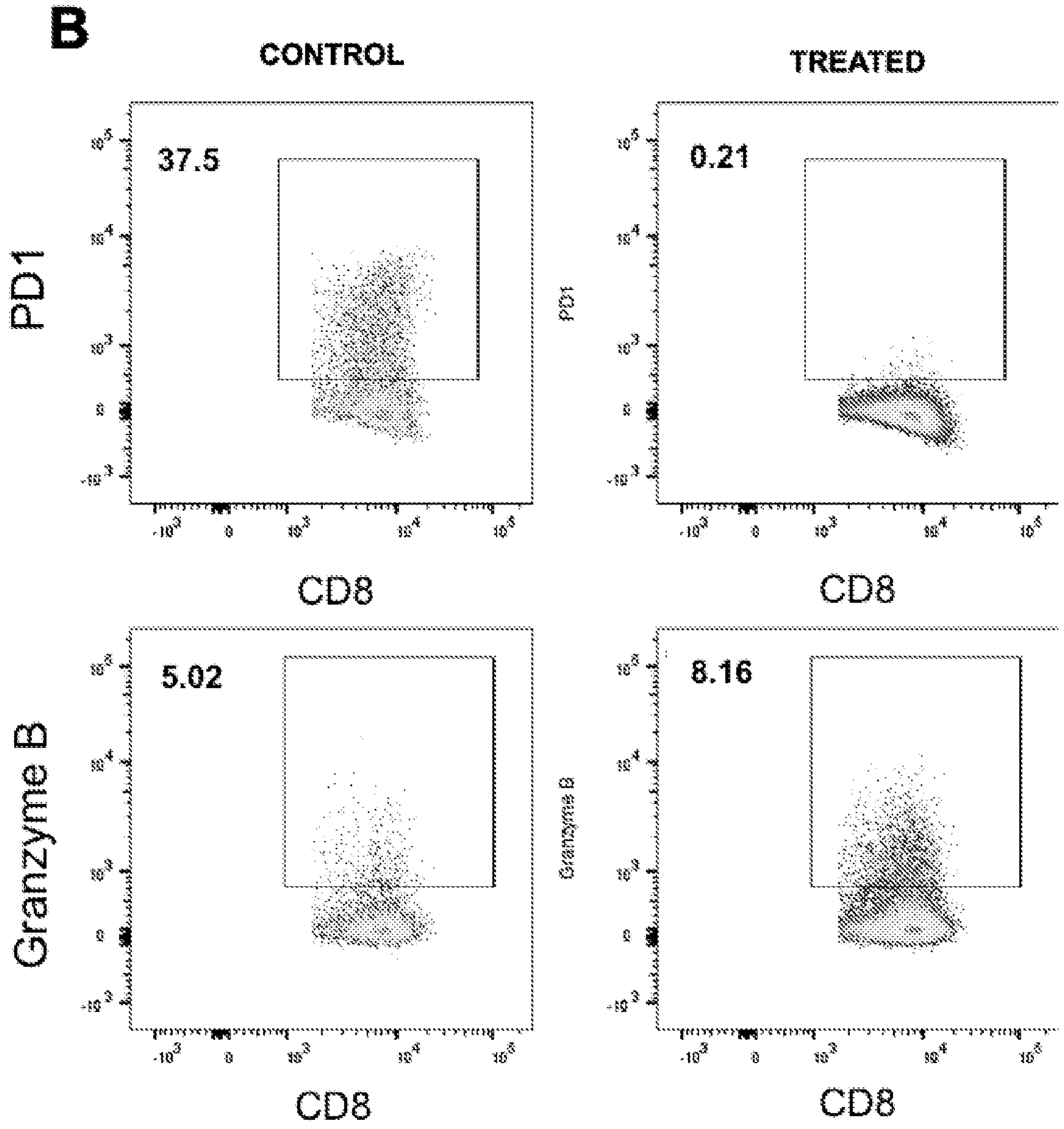
Figure 21:
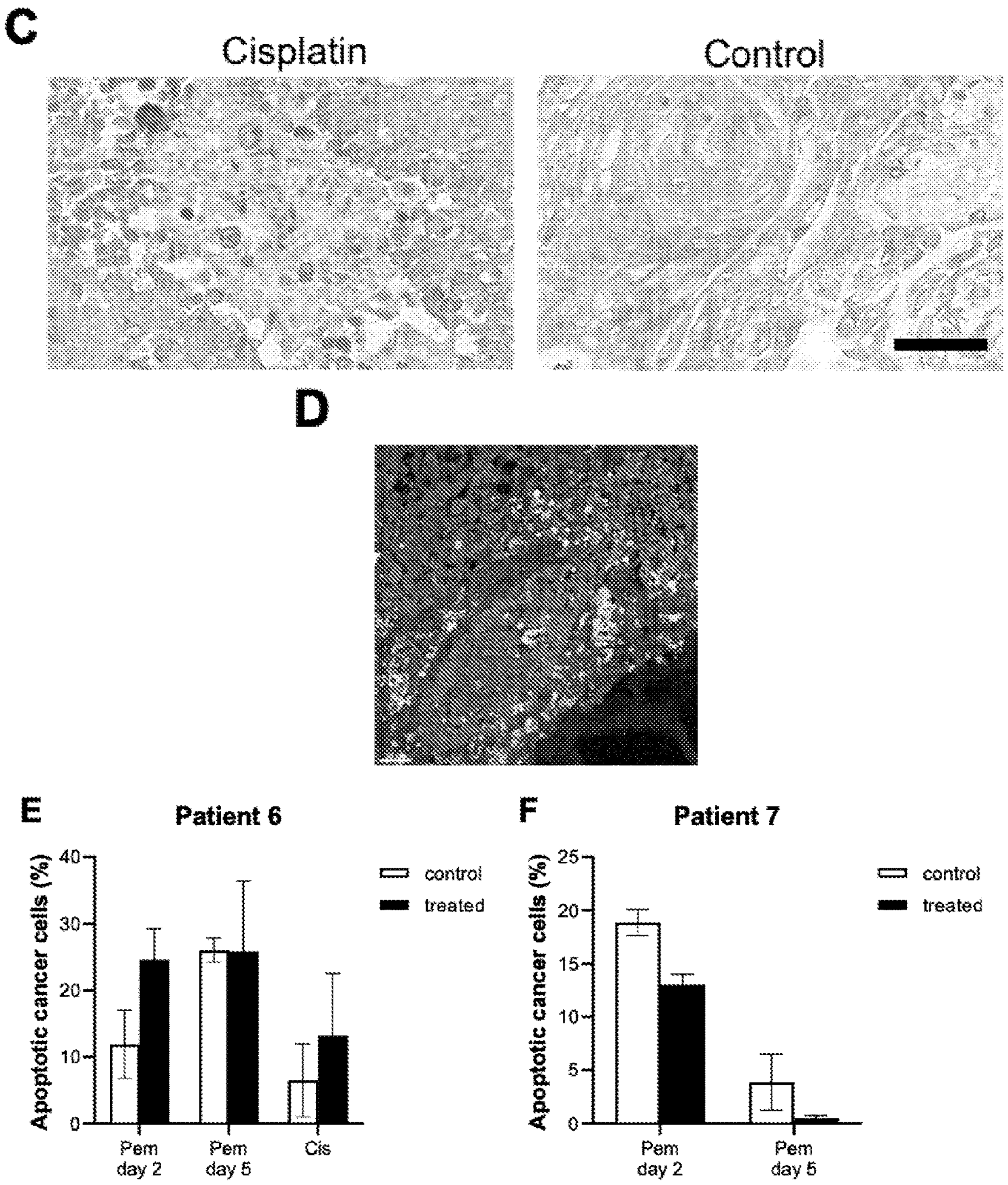

However, granzyme B slightly increased for another patient (FIG. 21B). Although no clinical correlation was able to be performed in the time-frame of this study, the results suggest that the engineered slice cultures using hydrogels are able to reflect inter-patient heterogeneity in response to immune checkpoint blockade. FIGS. 21C and D show that drug response readouts can be obtained by leveraging immunohistochemistry or immunofluorescence staining.

DISCUSSION

The importance of leveraging optimized biomaterials to enhance the preservation of patient-derived tumour slices as compared to the use of conventional plastic (PTFE) membrane inserts was demonstrated. Significantly, using a semi-synthetic hydrogel system to modulate stiffness and adhesivity, the dependency of tumour slice tissue integrity and molecular profile on material properties was observed. By culturing patient-derived tumour slices on integrin-binding hydrogels, the resulting engineered tumour slices not only maintain the original proportions of cancer and stromal cell populations, but also reflect inter-patient heterogeneity in response to immune checkpoint blockade.

Through altering the bulk polymer concentration to modulate hydrogel stiffness, the resulting differences in preservation of tumour slice area and morphology indicate the importance of optimizing material physical properties to maintain tissue integrity. As the loss of tissue integrity and architecture in the 1.25% HA hydrogels could also be attributed to the loss of hydrogel structure as a result of hydrogel degradation over time, work is ongoing our laboratories to probe the relationship between stiffness, hydrogel degradation and tumour slice integrity using non-degradable crosslinkers. Nevertheless, our results are consistent with previous studies reporting the importance of an underlying support to mechanically immobilize tumour slices ex vivo, without which, floating tissues lose architecture and viability (Davies et al., 2015). It was further observed that the presentation of RGD to engage integrins reduced the expression of pro-apoptotic genes as compared to the use of RDG. Furthermore, YAP activity was enhanced in the presence of RGD. Significantly, the powerful potential of leveraging tunable synthetic hydrogels to probe cell-ECM interactions that can maintain and potentially prolong tumour slice culture ex vivo was observed. This has never been shown, and cannot be done were naturally-derived matrices such as collagen or alginate gels used.

Although there have been many numerous reported studies on the development of tumour slice cultures, none have performed comprehensive characterization of tumour slice composition and molecular profile. In seeking to compare our engineered tumour slice cultures to those grown on conventional membrane inserts, deep characterization using scRNAseq was used. The enhanced preservation of cancer and stromal populations in the present engineered HA hydrogels clearly demonstrates the importance of leveraging biomaterials to augment current tumour slice culture methods, which are typically based on inert plastic membranes such as PTFE. The present findings demonstrate how manipulating tissue-biomaterial interactions may also control the behavior of cells present in tissue slices. That CAFs and myofibroblasts were maintained in the present engineered tumour slice cultures suggest the importance of providing integrin-binding sites to enable these mesenchymal cells to survive in vitro. Preservation of the immune and CAF populations and subpopulations (myofibroblastic CAFs and inflammatory CAFs) represents an unexpected finding that has important impact in the field of stromal biology intersecting with immuno-oncology. At present, there is a lack of preclinical in vitro and ex vivo tumour models that can recapitulate CAF heterogeneity found in patient tumours (Tang et al., 2021). Understanding and targeting CAF heterogeneity is now an important research strategy in overcoming resistance to immune checkpoint blockade (Harryvan et al., (2019). Accordingly, the present engineered tumour slice platform provides an urgently needed tool for validating CAF-targeting approaches either alone or in combination with immune checkpoint inhibitors.

Although predictive biomarkers (such as PD-L1 expression, immune signatures, and total mutational burden) that can predict the response of patients to immune checkpoint blockade exist, none are robustly predictive. It is likely that the complex and evolving TME determines ICI efficacy in each patient. Tumour explant cultures that maintain the original TME of patient tumours ex vivo enable the study of both baseline properties of a tumour and dynamics of treatment response. For example, Voabil et al., 2021 recently developed a patient-derived tumour fragment platform to elucidate the early immunological response (within 48 h) of human tumour tissue to ex vivo PD-1 blockade and determined biomarkers of response to immune checkpoint blockade. In a similar vein, the present tumour slice cultures can be leveraged to dissect changes that occur upon PD-1 blockade. The data provided herein suggests that the present engineered slice cultures are capable of reflecting inter-patient heterogeneity in response to PD-1 blockade that can be correlated to eventual patient outcome.

REFERENCES

Any listing or discussion of an apparently prior-published document in this specification should not necessarily be taken as an acknowledgement that such document is part of the state of the art or is common general knowledge.

- K. E. Bailey, C. Pino, M. L. Lennon, A. Lyons, J. G. Jacot, S. R. Lammers, M. Königshoff, C. M. Magin Embedding of Precision-Cut Lung Slices in Engineered Hydrogel Biomaterials Supports Extended Ex Vivo Culture, A J Respir Cell Mol Bio 62(1) (2020) 14-22.
- D. Bruni, H. K. Angell, J. Galon, The immune contexture and Immunoscore in cancer prognosis and therapeutic efficacy, Nat Rev Cancer 20(11) (2020) 662-680.
- C. M. Cattaneo, K. K. Dijkstra, L. F. Fanchi, S. Kelderman, S. Kaing, N. van Rooij, S. van den Brink, T. N. Schumacher, E. E. Voest, Tumour organoid-T-cell coculture systems, Nat Protoc 15(1) (2020) 15-39.
- E. J. Davies, M. Dong, M. Gutekunst, K. Narhi, H. J. van Zoggel, S. Blom, A. Nagaraj, T. Metsalu, E. Oswald, S. Erkens-Schulze, J. A. Delgado San Martin, R. Turkki, S. R. Wedge, T. M. af Hallstrom, J. Schueler, W. M. van Weerden, E. W. Verschuren, S. T. Barry, H. van der Kuip, J. A. Hickman, Capturing complex tumour biology in vitro: histological and molecular characterisation of precision cut slices, Sci Rep 5 (2015) 17187.
- J. Drost, H. Clevers, Organoids in cancer research, Nat Rev Cancer 18(7) (2018) 407-418.
- T. J. Harryvan, E. M. E. Verdegaal, J. C. H. Hardwick, L. Hawinkels, S. H. van der Burg, Targeting of the Cancer-Associated Fibroblast-T-Cell Axis in Solid Malignancies, J Clin Med 8(11) (2019).
- S. E. Hiemer, L. Zhang, V. K. Kartha, T. S. Packer, M. Almershed, V. Noonan, M. Kukuruzinska, M. V. Bais, S. Monti, X. Varelas, A YAP/TAZ-Regulated Molecular Signature Is Associated with Oral Squamous Cell Carcinoma, Mol Cancer Res 13(6) (2015) 957-68.
- I. R. Powley, M. Patel, G. Miles, H. Pringle, L. Howells, A. Thomas, C. Kettleborough, J. Bryans, T. Hammonds, M. MacFarlane, C. Pritchard, Patient-derived explants (PDEs) as a powerful preclinical platform for anti-cancer drug and biomarker discovery, Br J Cancer 122(6) (2020) 735-744.
- L. J. W. Tang, A. Zaseela, C. C. M. Toh, C. Adine, A. O. Aydar, N. G. Iyer, E. L. S. Fong, Engineering stromal heterogeneity in cancer, Adv Drug Deliv Rev 175 (2021) 113817.
- L. Tang Jia Wei, A. Zaseela, C. Toh, C. Adine, A. Omer Aydar, N. Gopalakrishna Iyer, E. Li Shan Fong, Engineering Stromal Heterogeneity in Cancer, Adv Drug Deliv Rev (2021).
- P. Voabil, M. de Bruijn, L. M. Roelofsen, S. H. Hendriks, S. Brokamp, M. van den Braber, A. Broeks, J. Sanders, P. Herzig, A. Zippelius, C. U. Blank, K. J. Hartemink, K. Monkhorst, J. Haanen, T. N. Schumacher, D. S. Thommen, An ex vivo tumor fragment platform to dissect response to PD-1 blockade in cancer, Nat Med 27(7) (2021) 1250-1261.

The invention claimed is:

1. A method for maintaining and/or culturing tissue slices; comprising:

(i) providing a tissue slice;

(ii) providing a hydrogel comprising conjugated peptides;

(iii) placing the tissue slice onto the hydrogel comprising conjugated peptides; and (iv) maintaining and/or culturing the tissue slice on the hydrogel using a culture medium, wherein the tissue slice is a tissue slice from a tumour, wherein step (iii) comprises placing the tissue slice on the hydrogel as crosslinking of the hydrogel takes place for achieving mechanical fixation of the tissue slice in the hydrogel, and wherein step (iv) comprises contacting the hydrogel with the culture medium, and wherein the hydrogel is substantially submerged with the culture medium and the tissue slice is partially submerged with the culture medium.

2. The method according to claim 1, wherein the hydrogel comprises a hyaluronan, collagen or gelatin modified with at least one chemical group.

3. The method according to claim 2, wherein the chemical group is for crosslinking the hydrogel.

4. The method according to claim 3, wherein the hydrogel comprises thiolated hyaluronan with conjugated peptides.

5. The method according to claim 1, wherein the peptides are for crosslinking the hydrogel and/or presenting/providing biochemical cues, and/or wherein the peptides comprise a peptide degradable by matrix metalloproteinases or other proteases.

6. The method according to claim 1, wherein the peptides comprise the sequence PQ.

7. The method according to claim 1, wherein the peptides comprises the sequence KGGGPQGIWGQGK (SEQ ID NO: 1) or a scrambled derivative.

8. The method according to claim 1, wherein the hydro gel further comprises at least one further set of peptides.

9. The method according to claim 8, wherein the at least one further set of peptides present/provide biochemical cues.

10. The method according to claim 8, wherein the at least one further set of peptides comprise one or more types of extracellular matrix protein or peptides comprising a peptide sequence derived from an extracellular matrix protein, and wherein the extracellular matrix protein comprises fibronectin, collagen and/or laminin.

11. The method according to claim 8, wherein the at least one further set of peptides comprises the sequence GRGDS (SEQ ID NO: 2) or a scrambled derivative.

12. The method according to claim 1, wherein the peptides comprise acrylated peptides.

13. The method according to claim 4, wherein attaining the desired stiffness of the hydrogel comprising conjugated peptide depends on the concentration of the hyaluronan in the hydro gel.

14. The method according to claim 4, wherein attaining the desired stiffness of the hydrogel comprises or further comprises increasing or decreasing the concentration of crosslinkers in the hydrogel.

15. The method according to claim 1, wherein the culture medium comprises at least one ROCK inhibitor.

16. The method according to claim 1, further comprising testing the effect of at least one therapeutic agent or potential therapeutic agent on the tissue slice.

* * * * *